US009339370B2

(12) United States Patent
Miniaci et al.

(10) Patent No.: US 9,339,370 B2
(45) Date of Patent: May 17, 2016

(54) APPARATUS AND METHOD FOR SEQUENTIALLY ANCHORING MULTIPLE GRAFT LIGAMENTS IN A BONE TUNNEL

(71) Applicant: THE CLEVELAND CLINIC FOUNDATION, Cleveland, OH (US)

(72) Inventors: Anthony Miniaci, Chagrin Falls, OH (US); Stephen D. Fening, Willoughby Hills, OH (US); Bret E. Hartzell, Canal Fulton, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 0 days.

(21) Appl. No.: 14/463,740

(22) Filed: Aug. 20, 2014

(65) Prior Publication Data
US 2015/0045886 A1       Feb. 12, 2015

Related U.S. Application Data

(63) Continuation-in-part of application No. 13/912,240, filed on Jun. 7, 2013, now Pat. No. 9,011,536, which is a continuation of application No. 12/765,444, filed on Apr. 22, 2010, now Pat. No. 8,491,652.

(60) Provisional application No. 61/171,518, filed on Apr. 22, 2009.

(51) Int. Cl.
*A61F 2/08*         (2006.01)
*E05C 5/04*        (2006.01)
(Continued)

(52) U.S. Cl.
CPC ....... *A61F 2/0811* (2013.01); *A61B 2017/0425* (2013.01); *A61B 2017/0429* (2013.01);
(Continued)

(58) Field of Classification Search
CPC .......... A61F 2/0811; A61F 2002/0835; A61F 2002/0817; A61F 2250/001
See application file for complete search history.

(56) References Cited

U.S. PATENT DOCUMENTS

| 1,146,651 A | * | 7/1915 | Raeger | .................. F16B 13/124 |
| | | | | 411/80.1 |
| 2,366,965 A | * | 1/1945 | Johnson | .............. F16B 19/1045 |
| | | | | 16/386 |

(Continued)

FOREIGN PATENT DOCUMENTS

| EP | 0232049 B1 | 1/1987 |
| EP | 0528573 A1 | 3/1992 |

(Continued)

OTHER PUBLICATIONS

Bergfeld et al., "Single- or Double-Bundle ACL Reconstruction: Technique vs. Concept", Orthopedics Today 2008, pp. 28-46.
(Continued)

*Primary Examiner* — Jacqueline Woznicki
(74) *Attorney, Agent, or Firm* — Tarolli, Sundheim, Covell & Tummino LLP

(57) ABSTRACT

An apparatus for anchoring elongate strands within a longitudinal tunnel is disclosed. At least two cams are arranged longitudinally adjacent each other along a longitudinal axis. A first anchor member includes a first cam-contacting surface and a first strand-contacting surface. The first cam-contacting surface is selectively operatively connected to a first cam. A second anchor member includes a second cam-contacting surface and a second strand-contacting surface. The second cam-contacting surface is selectively operatively connected to a second cam. An elongate strand is positioned between the tunnel wall and the first or second strand-contacting surfaces. Rotation of a selected cam causes the selected cam to selectively apply a force to a corresponding first or second cam-contacting surface to urge the corresponding first or second strand-contacting surface away from the longitudinal axis to produce frictional engagement of the elongate strand with both a tunnel wall and the first or second strand-contacting surface.

14 Claims, 16 Drawing Sheets

(51) Int. Cl.
*F16B 13/04* (2006.01)
*F16B 13/06* (2006.01)
*F16B 13/12* (2006.01)
*F16B 19/10* (2006.01)
*A61B 17/04* (2006.01)

(52) U.S. Cl.
CPC . *A61B2017/0438* (2013.01); *A61F 2002/0817* (2013.01); *A61F 2002/0823* (2013.01); *A61F 2002/0829* (2013.01); *A61F 2002/0835* (2013.01); *A61F 2002/0847* (2013.01); *A61F 2002/0852* (2013.01); *A61F 2002/0858* (2013.01); *A61F 2002/0876* (2013.01); *A61F 2002/0882* (2013.01); *A61F 2220/0008* (2013.01); *A61F 2250/001* (2013.01)

(56) References Cited

U.S. PATENT DOCUMENTS

| | | | | |
|---|---|---|---|---|
| 2,685,721 | A * | 8/1954 | Eves | F16B 5/06 411/15 |
| 3,022,701 | A * | 2/1962 | Potruch | F16B 13/126 411/80.1 |
| 3,213,745 | A * | 10/1965 | Dwyer | F16B 13/06 174/153 G |
| 3,301,123 | A * | 1/1967 | Worley | E21D 21/008 405/259.1 |
| 3,302,509 | A * | 2/1967 | Modrey | E21D 21/008 285/8 |
| 3,895,773 | A * | 7/1975 | Solo | F16B 15/04 248/546 |
| 4,176,428 | A * | 12/1979 | Kimura | B60R 13/0206 24/297 |
| 4,262,577 | A * | 4/1981 | Katz | F16B 13/00 29/525.04 |
| 4,637,765 | A * | 1/1987 | Omata | F16B 19/1081 411/41 |
| 4,662,808 | A * | 5/1987 | Camilleri | F16B 13/12 411/340 |
| 4,696,611 | A * | 9/1987 | Guay | F16B 19/02 411/103 |
| 4,797,046 | A * | 1/1989 | Ollivier | F16B 13/085 411/448 |
| 5,211,512 | A * | 5/1993 | Frischmann | F16B 13/068 405/259.4 |
| 5,234,430 | A * | 8/1993 | Huebner | A61B 17/8645 606/318 |
| 5,258,021 | A * | 11/1993 | Duran | A61F 2/2412 623/2.36 |
| 5,356,435 | A | 10/1994 | Thein | |
| 5,413,441 | A * | 5/1995 | Heminger | F16B 13/0825 411/107 |
| 5,480,403 | A * | 1/1996 | Lee | A61B 17/0401 606/232 |
| 5,562,376 | A * | 10/1996 | Fischer | F16B 13/0891 411/446 |
| 5,669,108 | A * | 9/1997 | Ferrari | A47B 88/044 16/383 |
| 5,702,397 | A | 12/1997 | Goble et al. | |
| 5,885,031 | A * | 3/1999 | White | E21D 21/008 405/259.1 |
| 5,916,216 | A | 6/1999 | DeSatnick et al. | |
| 6,186,716 | B1 * | 2/2001 | West | F16B 13/002 411/30 |
| 6,196,780 | B1 * | 3/2001 | Wakai | F16B 13/002 411/21 |
| 6,200,081 | B1 * | 3/2001 | Ferrari | E05D 5/0276 411/354 |
| 6,299,397 | B1 * | 10/2001 | Mengel | F16B 5/0092 411/24 |
| 6,562,071 | B2 | 5/2003 | Järvinen | |
| 6,632,245 | B2 | 10/2003 | Kim | |
| 7,008,451 | B2 | 3/2006 | Justin et al. | |
| 7,201,773 | B2 | 4/2007 | Steiner et al. | |
| 7,235,074 | B1 | 6/2007 | Sklar | |
| 7,326,247 | B2 | 2/2008 | Schmieding et al. | |
| 7,329,281 | B2 | 2/2008 | Hays et al. | |
| 8,545,535 | B2 * | 10/2013 | Hirotsuka | A61B 17/0401 606/232 |
| 9,133,871 | B2 * | 9/2015 | Schaeffer | F16B 13/065 |
| 2003/0144735 | A1 | 7/2003 | Sklar et al. | |
| 2004/0039447 | A1 * | 2/2004 | Simon | A61B 17/1604 623/13.11 |
| 2004/0260298 | A1 * | 12/2004 | Kaiser | A61F 2/0811 606/232 |
| 2005/0055027 | A1 * | 3/2005 | Yeung | A61B 17/0401 606/75 |
| 2006/0282085 | A1 * | 12/2006 | Stone | A61B 17/0401 604/500 |
| 2007/0156154 | A1 | 7/2007 | Schlienger et al. | |
| 2007/0162124 | A1 | 7/2007 | Whittaker | |
| 2008/0027430 | A1 | 1/2008 | Montgomery et al. | |
| 2008/0027542 | A1 * | 1/2008 | McQuillan | A61L 27/40 623/13.11 |
| 2008/0161806 | A1 | 7/2008 | Donnelly et al. | |
| 2008/0188897 | A1 * | 8/2008 | Krebs | A61B 17/7266 606/300 |
| 2008/0195204 | A1 | 8/2008 | Zhukauskas et al. | |
| 2008/0234819 | A1 | 9/2008 | Schmieding et al. | |
| 2010/0274356 | A1 * | 10/2010 | Fening | A61F 2/0811 623/13.14 |
| 2015/0045886 | A1 * | 2/2015 | Miniaci | A61F 2/0811 623/13.14 |

FOREIGN PATENT DOCUMENTS

| | | |
|---|---|---|
| WO | 8809157 A1 | 12/1988 |
| WO | 9818409 A1 | 5/1998 |
| WO | 0130253 A1 | 5/2001 |
| WO | 2005051205 A1 | 6/2005 |
| WO | 2007109769 A1 | 9/2007 |

OTHER PUBLICATIONS

Wu et al., "Tension Patterns of the Anteromedial and Posterolateral Grafts in a Double-Bundle Anterior Cruciate Ligament Reconstruction", Journal of Orthopaedic Research, 2009, vol. 27, pp. 879-884.
International Search Report, dated Jul. 2, 2010, pp. 1-6.

* cited by examiner

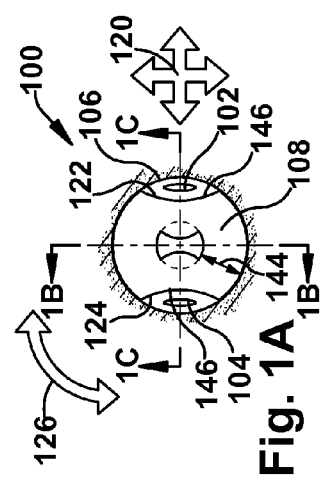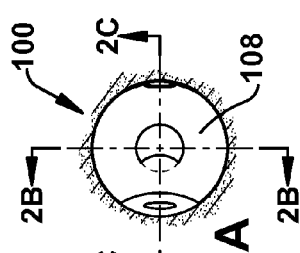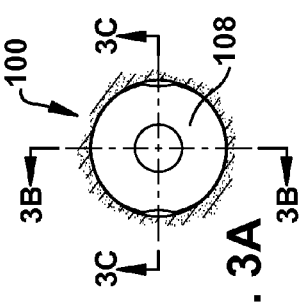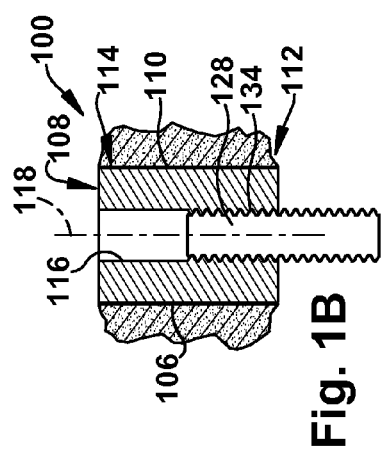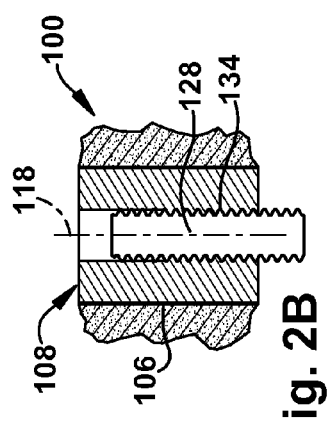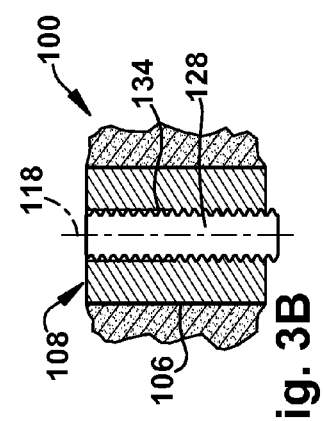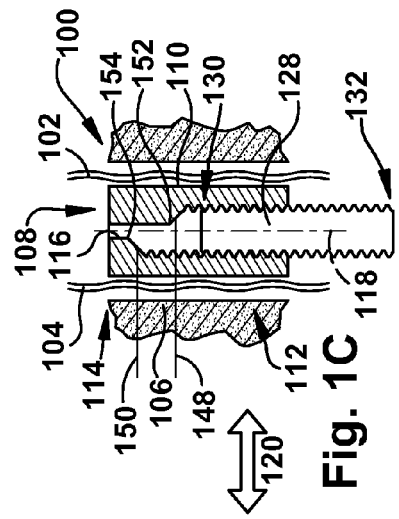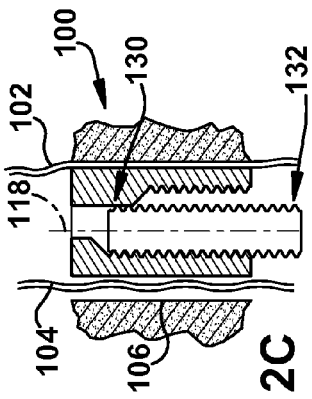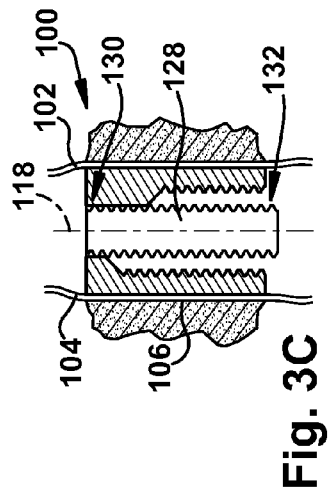

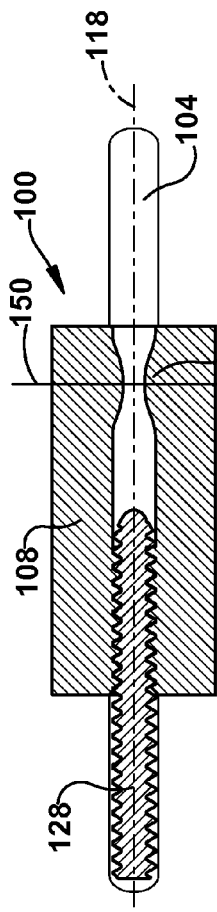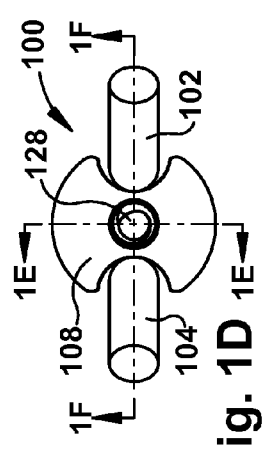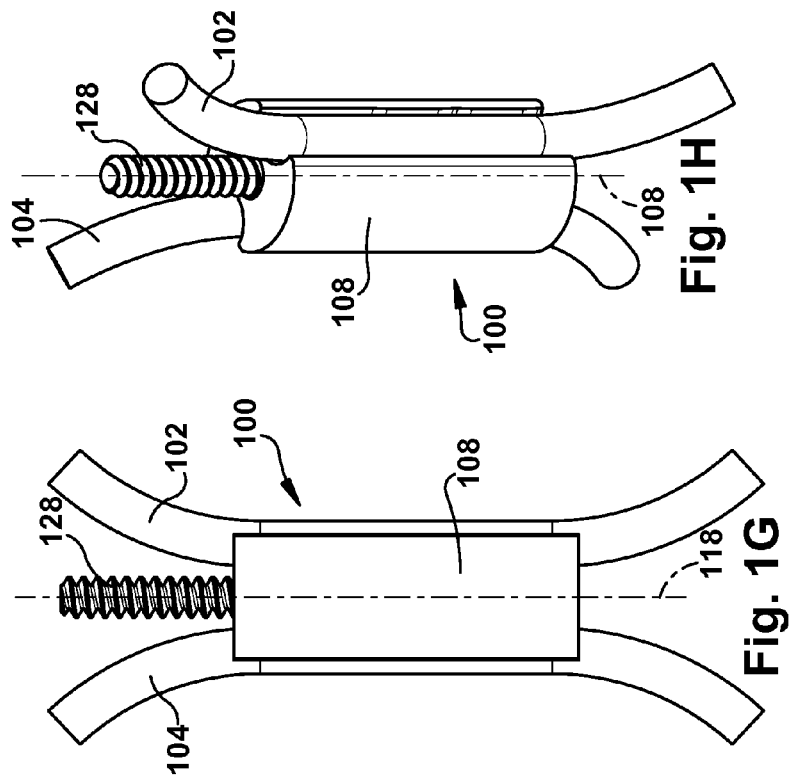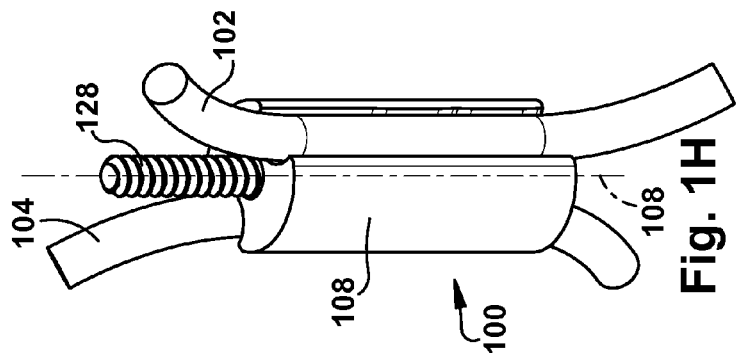

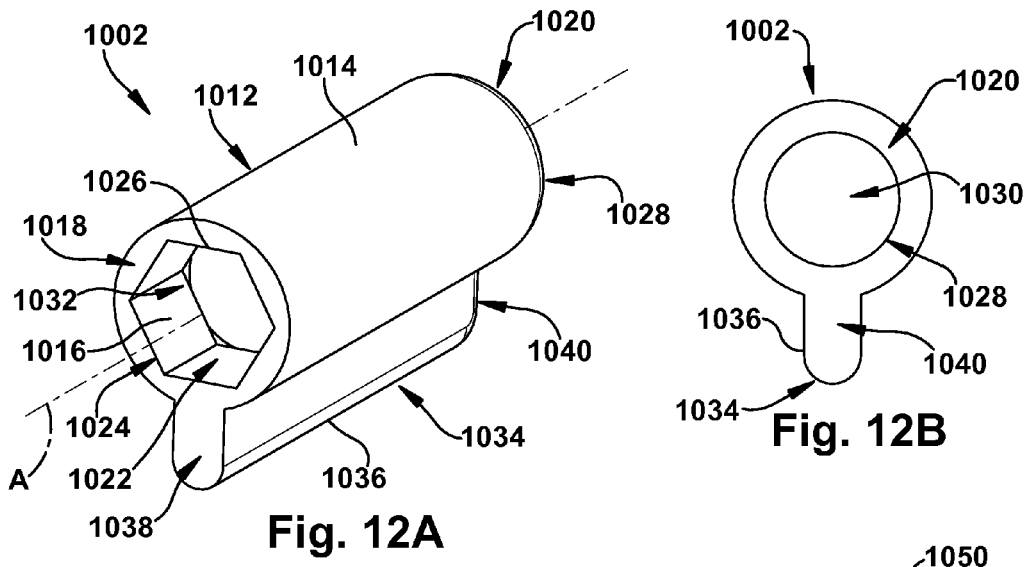
Fig. 12A
Fig. 12B
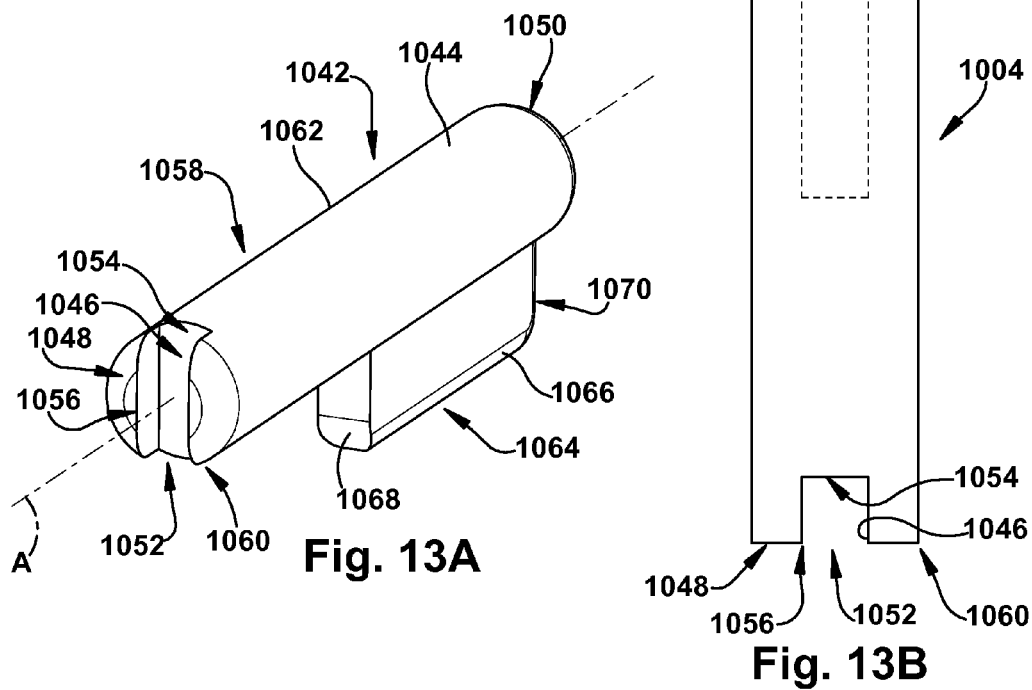
Fig. 13A
Fig. 13B

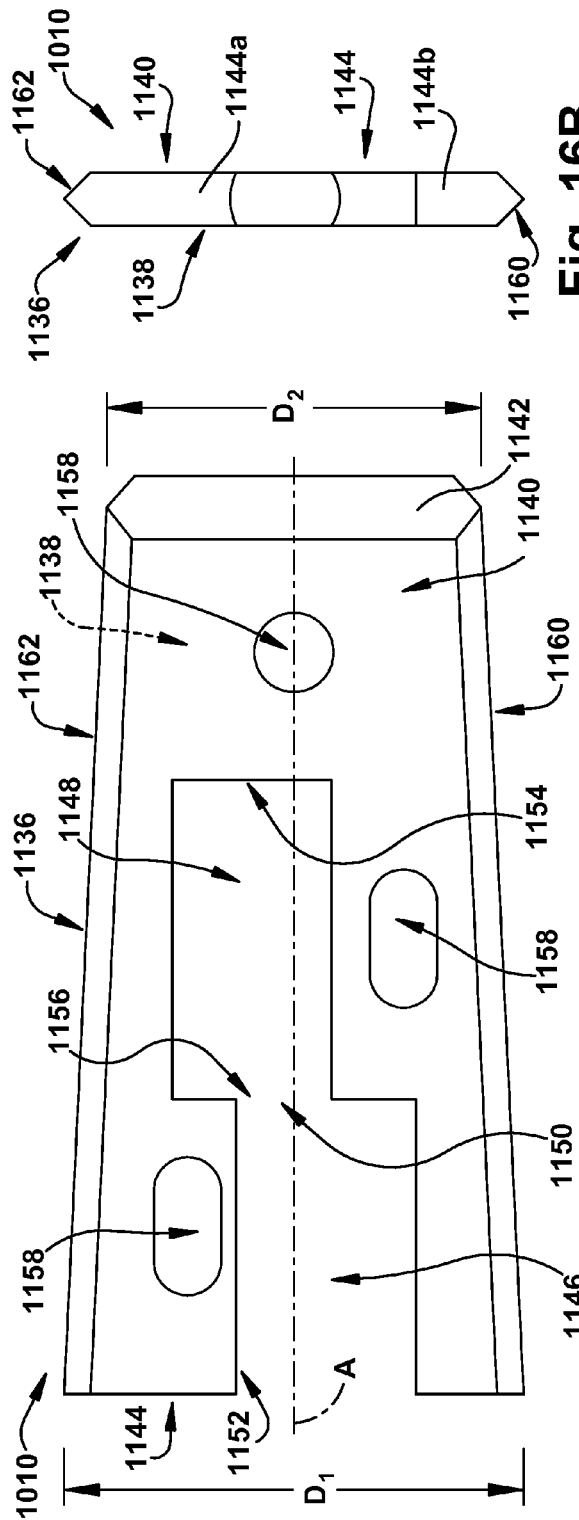
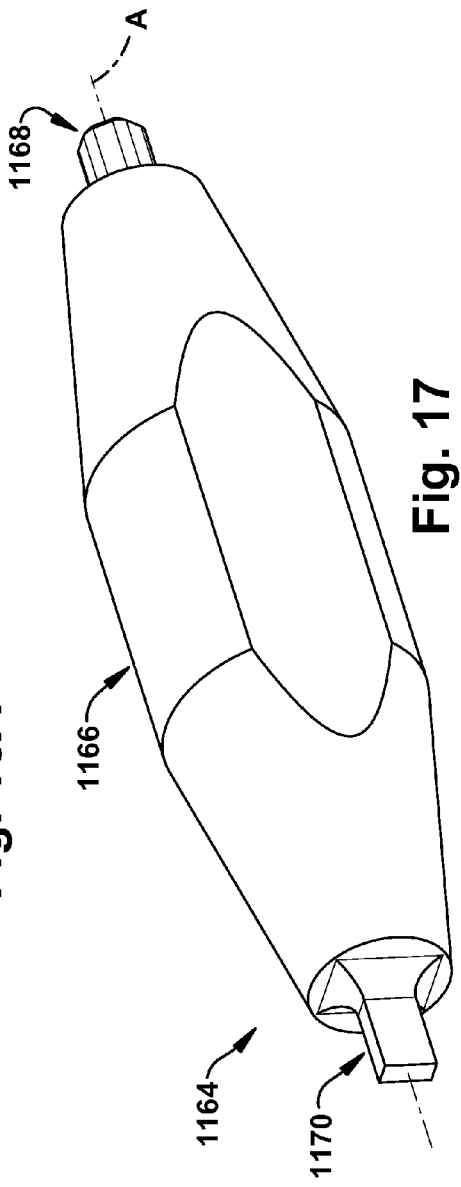
Fig. 16B
Fig. 16A
Fig. 17

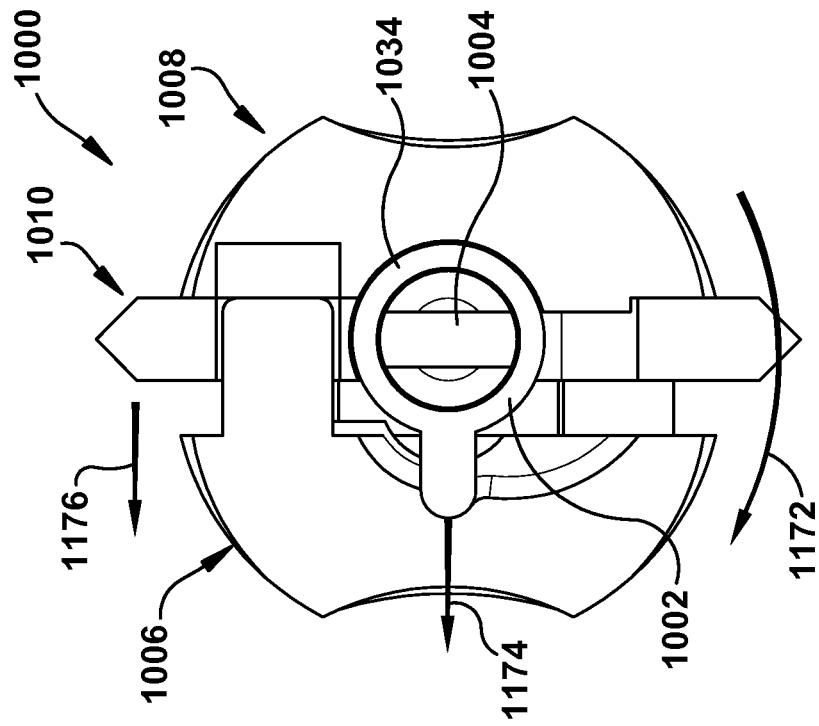
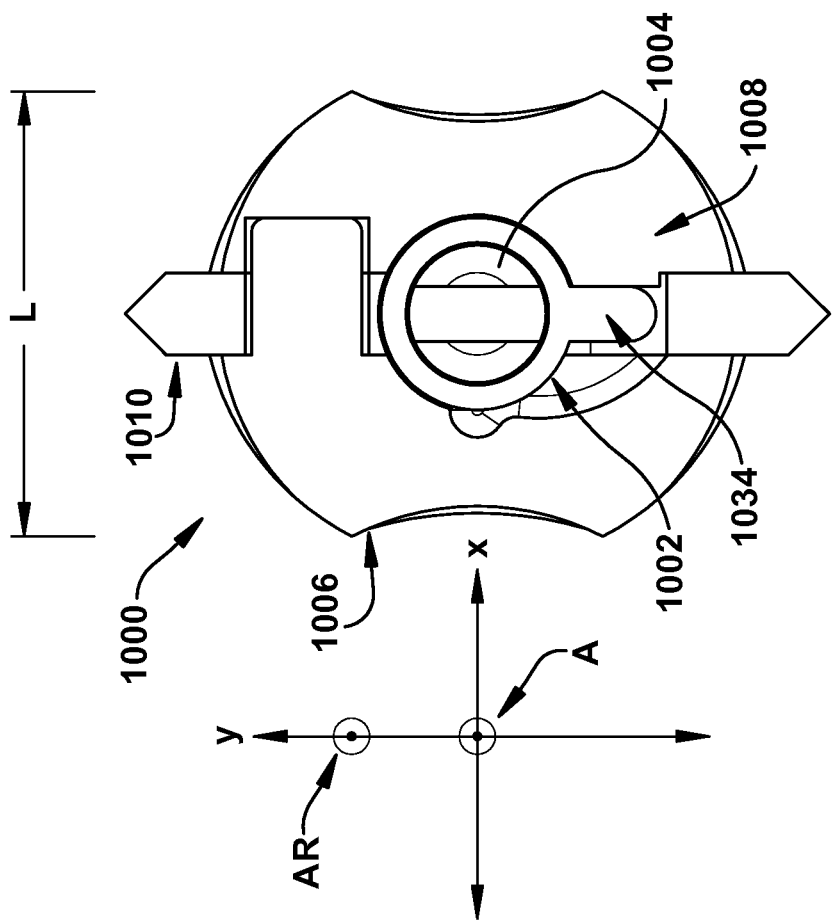

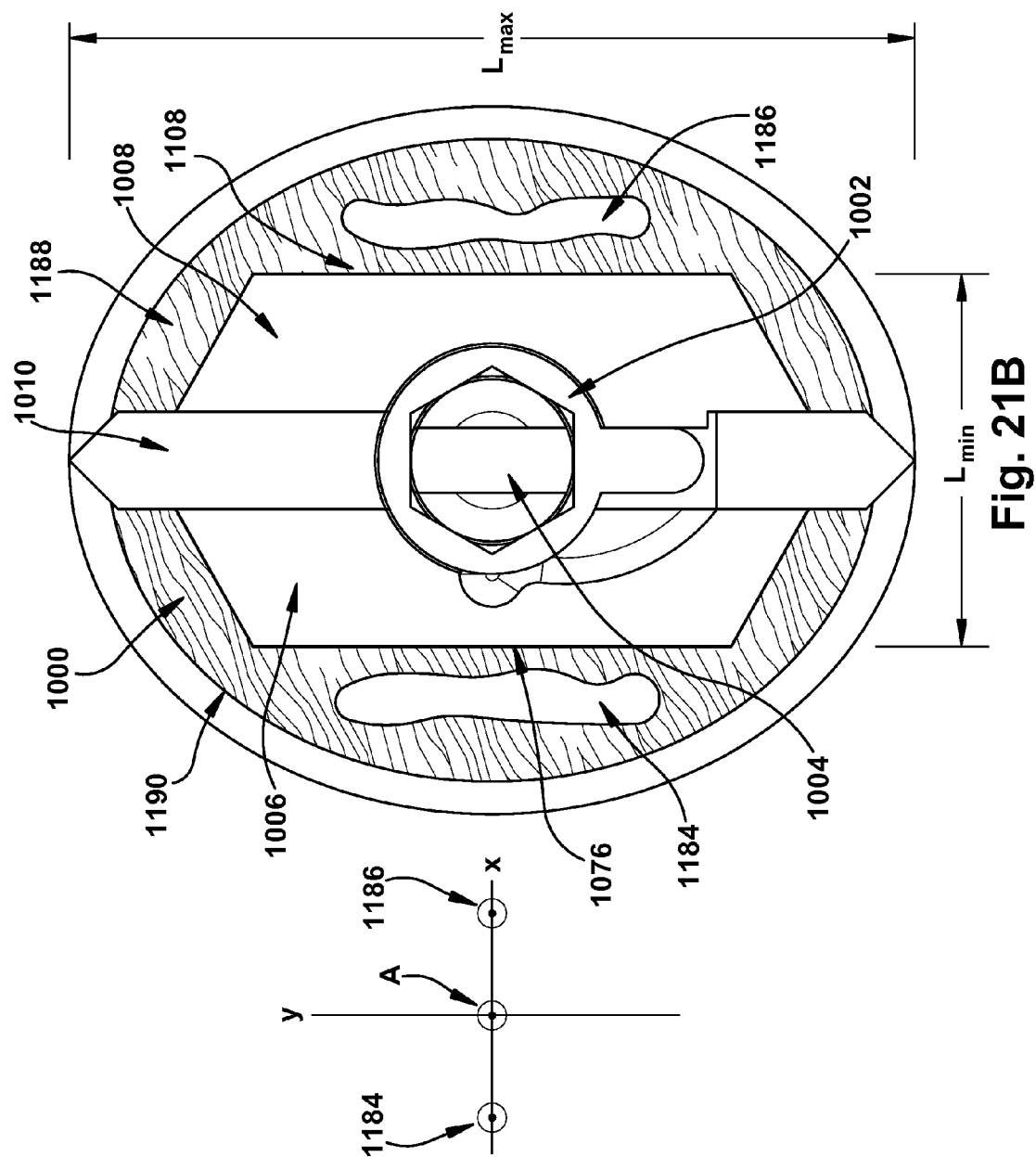

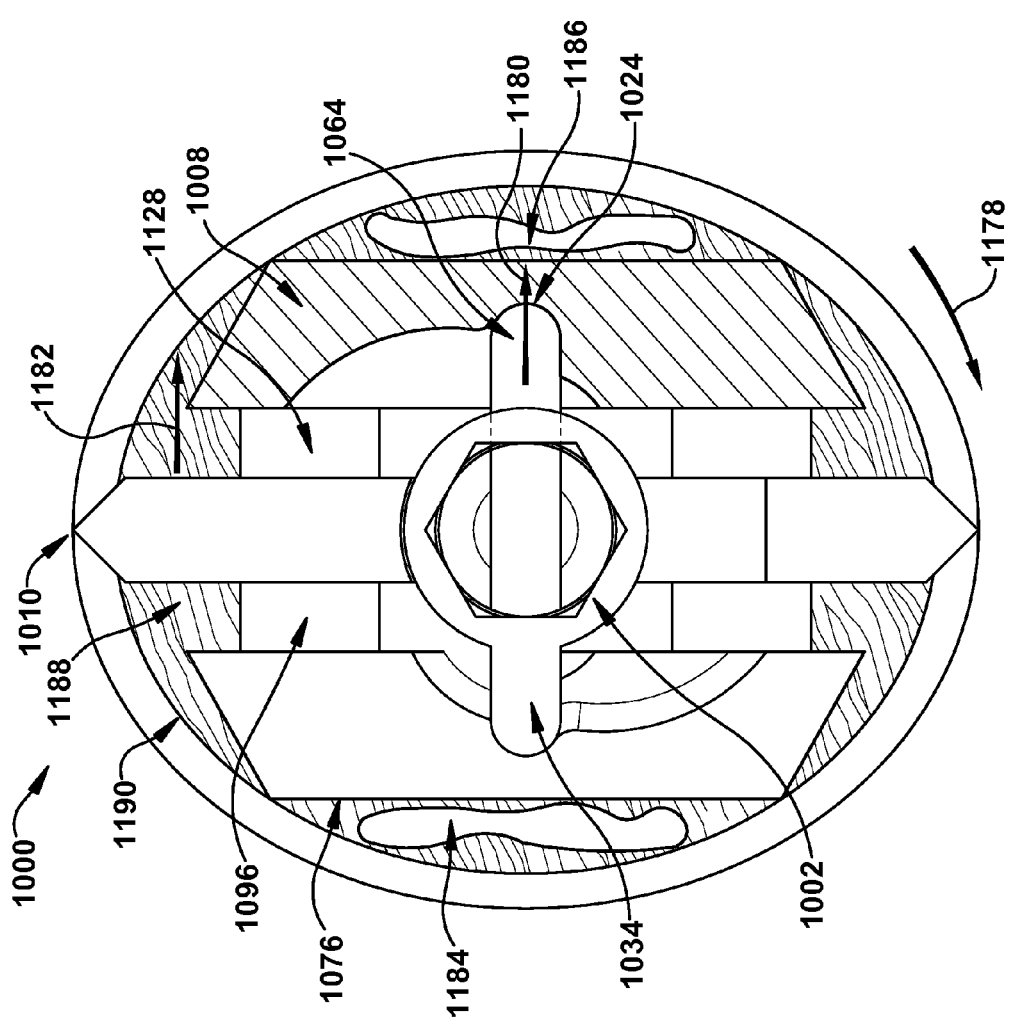

APPARATUS AND METHOD FOR SEQUENTIALLY ANCHORING MULTIPLE GRAFT LIGAMENTS IN A BONE TUNNEL

RELATED APPLICATION

This application is a continuation-in-part of U.S. patent application Ser. No. 13/912,240, filed 7 Jun. 2013, which is a continuation of U.S. patent application Ser. No. 12/765,444, filed 22 Apr. 2010 (now U.S. Pat. No. 8,491,652, issued 23 Jul. 2013), which claims priority from U.S. Provisional Application No. 61/171,518, filed Apr. 22, 2009, each of which is incorporated herein by reference in its entirety.

TECHNICAL FIELD

The present invention relates to an apparatus and method for anchoring graft ligaments and, more particularly, to an apparatus and method for sequentially anchoring multiple graft ligaments in a bone tunnel.

BACKGROUND OF THE INVENTION

Ligaments are tough bands of tissue which serve to connect the articular extremities of bones, or to support or retain organs in place within the body. Ligaments are typically composed of coarse bundles of dense fibrous tissue which are disposed in a parallel or closely interlaced manner, with the fibrous tissue being pliant and flexible, but not significantly extensible. Ligaments may be torn or ruptured as a result of trauma. As a result, various procedures have been developed to repair or replace such damaged ligaments.

For example, in the human knee, the anterior and posterior cruciate ligaments extend between the top end of the tibia and the bottom end of the femur. The anterior and posterior cruciate ligaments cooperate, together with other ligaments and soft tissue, to provide both static and dynamic stability to the knee. Often, the anterior cruciate ligament (hereafter, the "ACL") is ruptured or torn as a result of, for example, a sports-related injury. Consequently, various surgical procedures have been developed for reconstructing the ACL so as to restore normal function to the knee.

In many examples, the ACL may be reconstructed by replacing the ruptured ACL with a graft ligament. More particularly, with such procedures, bone tunnels are typically formed in the top end of the tibia and the bottom end of the femur, with one end of the graft ligament being positioned in the femoral tunnel and the other end of the graft ligament being positioned in the tibial tunnel. The two ends of the graft ligament are anchored in place in various ways known in the art so that the graft ligament extends between the femur and the tibia in substantially the same way, and with substantially the same function, as the original ACL. This graft ligament then cooperates with the surrounding anatomical structures so as to restore normal function to the knee.

In some circumstances, the graft ligament may be a ligament or tendon which is harvested from elsewhere in the patient (autograft) or from a cadaveric donor (allograft) (e.g., a hamstring); in other circumstances, the graft ligament may be a synthetic device. For the purposes of the following description, all of these types of ACL-replacing tissues will be collectively referred to as a "graft ligament".

The native ACL is not simply a band of connective tissue, but has a complex and partially twisted "double-bundle" structure in which an anteromedial portion/bundle of the ACL controls the forward-backward pivoting of the joint, and a posterolateral portion/bundle of the ACL controls rotational stability of the joint. When the knee is straight, these two bundles extend in a parallel manner between the femur and tibia. When the knee is flexed, the two bundles cross each other. The anteromedial and posterolateral bundles are subtly different in the manner in which they mechanically interact with each other and with other components of a healthy knee joint. For example, the anteromedial and posterolateral bundles may be under different amounts and/or directions of tensile force within the knee joint. It is common for patients with ACL injuries to have damage to both the anteromedial and posterolateral bundles.

Traditionally, a single graft ligament has been used to restore knee function to the patient by merely approximating the function of the native ACL. A single-graft technique involves drilling a single bone tunnel in each of the femur and tibia. This technique is well-established in the art and is considered a routine surgical procedure, after which patients typically return to their normal level of activity. However, a single-graft reconstruction does not reflect the original knee structure and therefore might lead to future adverse effects due to long-term use of the knee in a mechanically different configuration than the native anatomy.

In the last several years, surgeons have begun to refine their techniques to better mimic the double-bundle structure of the native ACL, as well, in the interest of creating a more "natural" replacement ACL and with the goal of a better long-term prognosis for achieving normal function of the reconstructed knee joint. One currently used double-bundle ACL replacement technique requires separate bone tunnels to be provided for each of the two reconstructive grafts. However, drilling two tunnels in close proximity is technically difficult and brings about a heightened risk of complication.

In a variation on this known technique, the two graft ligaments replacing the anteromedial and posterolateral bundles of the ACL both run from a single femoral bone tunnel to a single tibial bone tunnel. Due to the limited confines of the bone tunnels, traditional graft-anchoring techniques may not be effective in placing dual graft ligaments within a single tunnel. An example of a commercially available system which has been developed to address the specialized anchoring needs of a double-bundle ACL replacement is the AperFix™ system, available from Cayenne Medical of Scottsdale, Ariz. However, the AperFix™ product is limited in the manner in which each of the two graft ligaments may be manipulated (requiring a substantially symmetrical and simultaneous placement, tensioning, and anchoring of these two graft ligaments) and in aligning the bundles to replicate the placement of a native ACL within a single tunnel. Therefore, the graft ligaments used with currently available double- or single-tunnel systems do not, and may not, accurately approximate the complex and individually varying mechanical interactions of the anteromedial and posterolateral bundles of a native ACL.

SUMMARY OF THE INVENTION

In an embodiment of the present invention, an apparatus for anchoring at least two graft ligaments within a longitudinal bone tunnel is described. A longitudinal sleeve has at least two radially spaced ligament-contacting surfaces located in lateral opposition to a sleeve inner lumen. The sleeve is configured for at least partial insertion into the bone tunnel with each graft ligament positioned laterally adjacent a different ligament-contacting surface. The graft ligaments are at least partially located between the bone tunnel and the sleeve. An actuating member has longitudinally separated proximal and distal actuating member ends. An asymmetrically offset profile is defined by at least one of the sleeve and the actuating member. The asymmetrically offset profile has a plurality of longitudinally spaced engagement thresholds. The actuating member is inserted longitudinally into the sleeve to cause frictional engagement of each graft ligament with both the bone tunnel and at least one ligament-contacting surface. The frictional engagement of each graft ligament is temporally spaced apart from the frictional engagement of at least one other graft ligament. The temporal spacing is provided by the plurality of engagement thresholds.

In an embodiment of the present invention, a method of anchoring at least two longitudinally extending graft ligaments within a bone tunnel during replacement of a native ACL is described. A first graft ligament is extended longitudinally through the bone tunnel. A second graft ligament is extended longitudinally through the bone tunnel at a location radially spaced apart from the first graft ligament. A sleeve is provided, the sleeve having a sleeve outer surface and longitudinally separated proximal and distal sleeve ends with a sleeve inner lumen extending therebetween. The sleeve is placed longitudinally within the bone tunnel with at least a portion of each of the first and second graft ligaments being located laterally between the sleeve outer surface and the bone tunnel. An actuating member is provided, the actuating member having an actuating member outer surface and longitudinally separated proximal and distal actuating member ends. An asymmetrically offset profile is defined in the longitudinal direction with at least one of the sleeve inner lumen and the actuating member outer surface. The asymmetrically offset profile defines longitudinally spaced first and second engagement thresholds. At least a portion of the actuating member is longitudinally inserted into the sleeve inner lumen. The actuating member is advanced distally into the sleeve inner lumen. A first predetermined tensile force is applied to the first graft ligament. The actuating member is advanced with respect to the sleeve, bringing at least a portion of both the actuating member and the sleeve laterally adjacent to the first engagement threshold to cause the first graft ligament to frictionally engage the sleeve outer surface and the bone tunnel. A second predetermined tensile force is applied to the second graft ligament. The actuating member is advanced with respect to the sleeve, bringing at least a portion of both the actuating member and the sleeve laterally adjacent to the second engagement threshold to cause the second graft ligament to frictionally engage the sleeve outer surface and the bone tunnel after the first graft ligament has frictionally engaged the sleeve outer surface and the bone tunnel.

In an embodiment of the present invention, a sequentially-actuated graft anchor system for use in anchoring at least two longitudinally extending graft ligaments within a bone tunnel during replacement of a native anterior cruciate ligament ("ACL") is described. A sleeve has a sleeve outer surface and longitudinally separated proximal and distal sleeve ends with a sleeve inner lumen extending therebetween. The sleeve defines a longitudinal axis, and the sleeve is adapted for longitudinal placement within the bone tunnel with at least a portion of the at least two graft ligaments being located laterally between the sleeve outer surface and the bone tunnel. An actuating member has an actuating member outer surface and longitudinally separated proximal and distal actuating member ends. At least a portion of the actuating member is adapted for selective longitudinal insertion into the sleeve inner lumen. At least one of the sleeve inner lumen and the actuating member outer surface defines an asymmetrically offset profile in the longitudinal direction. The asymmetrically offset profile has longitudinally spaced first and second engagement thresholds. Distal advancement of the actuating member into the sleeve inner lumen with respect to the sleeve, bringing at least a portion of both the actuating member and the sleeve laterally adjacent to the first engagement threshold causes a first one of the at least two graft ligaments to frictionally engage the sleeve outer surface and the bone tunnel before distal advancement of the actuating member into the sleeve inner lumen with respect to the sleeve, bringing at least a portion of both the actuating member and the sleeve laterally adjacent to the second engagement threshold causes a second one of the at least two graft ligaments to frictionally engage the sleeve outer surface and the bone tunnel.

According to an embodiment of the present invention, an apparatus for anchoring at least two elongate strands within a longitudinal tunnel that has a tunnel wall is disclosed. The apparatus includes a longitudinal axis. At least two cams are arranged longitudinally adjacent each other along the longitudinal axis. A first anchor member has a first anchor member body. The first anchor member is laterally spaced from the longitudinal axis. The first anchor member extends in a first lateral direction with respect to the longitudinal axis. The first anchor member includes a first cam-contacting surface disposed on a portion of the first anchor member body. A first strand-contacting surface is disposed on a portion of the first anchor member body laterally spaced from the first cam-contacting surface. The first cam-contacting surface is selectively operatively connected to a first one of the at least two cams. A second anchor member has a second anchor member body. The second anchor member is laterally spaced from the longitudinal axis. The second anchor member extends in a second lateral direction with respect to the longitudinal axis. The second lateral direction is different from the first lateral direction. The second anchor member includes a second cam-contacting surface disposed on a portion of the second anchor member body. A second strand-contacting surface is disposed on a portion of the second anchor member body that is laterally spaced from the second cam-contacting surface. The second cam-contacting surface is selectively operatively connected to a second one of the at least two cams. At least a portion of at least one first elongate strand is positioned substantially parallel to the longitudinal axis and is interposed laterally between the tunnel wall and at least a portion of the first strand-contacting surface. At least a portion of at least one second elongate strand is positioned substantially parallel to the longitudinal axis and is interposed laterally between the tunnel wall and at least a portion of the second strand-contacting surface. Rotation of a selected cam about an axis of rotation that is substantially parallel to the longitudinal axis produces pivotal movement of at least a portion of the selected cam about the longitudinal axis. The pivotal movement of the portion of the selected cam causes the pivotally-moving portion of the selected cam to selectively apply a force to at least a portion of a corresponding first or second cam-contacting surface to urge the corresponding first or second strand-contacting surface away from the longitudinal axis in the corresponding first or second lateral direction to produce frictional engagement of at least one corresponding elongate strand with both the tunnel wall and the corresponding first or second strand-contacting surface.

According to an embodiment of the present invention, an apparatus for anchoring at least two elongate strands within a longitudinal tunnel that has a tunnel wall is disclosed. The apparatus includes a longitudinal axis. A first cam has a first cam driver-engaging feature disposed on a distal first cam surface. A first cam-engaging feature is disposed on a proximal first cam surface. A first cam flange is disposed on an outer first cam surface. A second cam has a second cam driver-engaging feature disposed on a distal second cam surface. A second cam-engaging feature is disposed on a proximal second cam surface. A second cam flange is disposed on an outer second cam surface. At least a portion of the first cam-engaging surface engages at least a portion of the second cam-engaging surface to maintain a longitudinal arrangement of the first and second cams such that the first and second cam driver-engaging features are substantially longitudinally aligned along the longitudinal axis. A first anchor member has a first anchor member body. The first anchor member is laterally spaced from the longitudinal axis along a first lateral direction extending outwardly from the longitudinal axis. The first anchor member includes a first cam-contacting surface disposed a portion of the first anchor member body. A first strand-contacting surface is disposed on a portion of the first anchor member body that is laterally opposite the first cam-contacting surface. The first cam flange selectively engages at least a portion of the first cam-contacting surface. A second anchor member has a second anchor member body. The second anchor member is laterally spaced from the longitudinal axis along a second lateral direction extending outwardly away from the longitudinal axis. The second lateral direction is substantially opposite the first lateral direction. The second anchor member includes a second cam-contacting surface disposed on a portion of the second anchor member body. A second strand-contacting surface is disposed on a portion of the second anchor member body laterally opposite the second cam-contacting surface. The second cam flange selectively engages at least a portion of the second cam-contacting surface. At least a portion of at least one first elongate strand is positioned substantially parallel to the longitudinal axis and is interposed laterally between the tunnel wall and at least a portion of the first strand-contacting surface. At least a portion of at least one second elongate strand is positioned substantially parallel to the longitudinal axis and is interposed laterally between the tunnel wall and at least a portion of the second strand-contacting surface. Rotation of each of the first and second cams about an axis of rotation that is substantially parallel to the longitudinal axis produces pivotal movement of the corresponding first and second cam flanges about the longitudinal axis. The pivotal movement of the first and second cam flanges causes the first and second cam flanges to selectively apply a force to at least a portion of a corresponding first and second cam-contacting surfaces to urge the corresponding first and second strand-contacting surfaces away from the longitudinal axis in the corresponding first and second lateral directions to produce frictional engagement of at least one elongate strand with both the tunnel wall and the corresponding first and second strand-contacting surfaces.

According to an embodiment of the present invention, a method of anchoring at least one elongate strand within a longitudinal tunnel having a tunnel wall is disclosed. An anchor apparatus that has a longitudinal axis that is substantially parallel with the longitudinal tunnel is provided. The anchor apparatus includes laterally spaced first and second anchor members and a cam that has a cam flange. The first anchor member includes a first anchor member body with a first cam-contacting surface and an oppositely disposed first strand-contacting surface. The first anchor member is laterally spaced from the longitudinal axis in a first lateral direction with the respect to the longitudinal axis. The second anchor member includes a second anchor member body with a second cam-contacting surface and an oppositely disposed second strand-contacting surface. The second anchor member is laterally spaced from the longitudinal axis in a second lateral direction with respect to the longitudinal axis. The second lateral direction is substantially angularly offset from the first lateral direction. The cam is operably connected to at least one of the first and second cam-contacting surfaces. The anchor apparatus is inserted into the longitudinal tunnel. At least one elongate strand is positioned at least partially parallel to the longitudinal axis such that the at least one elongate strand is interposed laterally between the tunnel wall and at least a portion of a selected one of the first and second strand-contacting surfaces. The cam is rotated such that the cam flange moves pivotally about the longitudinal axis and applies a force to at least a portion of a selected one of the first or second cam-contacting surfaces to urge the selected one of the first or second strand-contacting surface away from the longitudinal axis in the corresponding first or second lateral direction to produce frictional engagement of at least one elongate strand with both the tunnel wall and the corresponding first or second strand-contacting surface.

According to an embodiment of the present invention, a method of anchoring at least one elongate strand within a longitudinal tunnel that has a tunnel wall is disclosed. An anchor apparatus that has a longitudinal axis that is substantially coaxial with the longitudinal tunnel is provided. The anchor apparatus includes laterally spaced first and second anchor members and longitudinally spaced first and second cams. The first anchor member includes a first anchor member body with a first cam-contacting surface and an oppositely disposed first strand-contacting surface. The first anchor member is laterally spaced from the longitudinal axis in a first lateral direction with respect to the longitudinal axis. The second anchor member includes a second anchor member body with a second cam-contacting surface and an oppositely disposed second strand-contacting surface. The second anchor member is laterally spaced from the longitudinal axis in a second lateral direction with respect to the longitudinal axis. The second lateral direction is substantially opposite the first lateral direction. The first cam is selectively operatively connected to the first cam-contacting surface. The first cam has a first cam flange and a first cam driver-engaging feature. The second cam is selectively operatively connected to the second cam-contacting surface. The second cam has a second cam flange and a second cam driver-engaging feature. The anchor apparatus is inserted into the longitudinal tunnel. At least one elongate strand is positioned at least partially parallel to the longitudinal axis such that the at least one elongate strand is interposed laterally between the tunnel wall and at least a portion of a selected one of the first and second strand-contacting surfaces. The first cam is rotated such that the first cam flange pivotally moves about the longitudinal axis. A force is applied to a portion of the first cam-contacting surface to urge the first strand-contacting surface away from the longitudinal axis in the first lateral direction when the first cam is rotated. The pivotal movement of the first cam applies a first laterally-oriented force to at least one stop disposed on a portion of the first cam-contacting surface to urge the first strand-contacting surface away from the longitudinal axis in the first lateral direction. Frictional engagement of at least one elongate strand with both the tunnel wall and the first strand-contacting surface is produced when the first-strand contacting surface moves in the first lateral direction. The second cam is rotated such that the second cam flange pivotally moves about the longitudinal axis. A force is applied to a portion of the second cam-contacting surface to urge the second strand-contacting surface away from the longitudinal axis in the second lateral direction when the second cam is rotated. The pivotal movement of the second cam applies a second laterally-oriented force to at least one stop disposed on a portion of the second cam-contacting surface to urge the second strand-contacting surface away from the longitudinal axis in the second lateral direction. Frictional engagement of at least one elongate strand with both the tunnel wall and the second strand-contacting surface is produced when the second-strand contacting surface moves in the second lateral direction.

BRIEF DESCRIPTION OF THE DRAWINGS

For a better understanding of the invention, reference may be made to the accompanying drawings, in which:

FIG. 1A is a schematic top view of an embodiment of the present invention in a first condition;

FIG. 1B is a cross-section taken along line 1B-1B of FIG. 1A;

FIG. 1C is a cross-section taken along line 1C-1C of FIG. 1A;

FIG. 1D is a top view of the embodiment of FIG. 1A;

FIG. 1E is a cross-section taken along line 1E-1E of FIG. 1D;

FIG. 1F is a cross-section taken along line 1F-1F of FIG. 1D;

FIG. 1G is a side view of the embodiment of FIG. 1D;

FIG. 1H is a perspective view of the embodiment of FIG. 1D;

FIG. 2A is a schematic top view of the embodiment of FIG. 1A in a second condition;

FIG. 2B is a cross-section taken along line 2B-2B of FIG. 2A;

FIG. 2C is a cross-section taken along line 2C-2C of FIG. 2A;

FIG. 3A is a schematic top view of the embodiment of FIG. 1A in a third condition;

FIG. 3B is a cross-section taken along line 3B-3B of FIG. 3A;

FIG. 3C is a cross-section taken along line 3C-3C of FIG. 3A;

FIG. 12A is a perspective side view of a component of the embodiment of FIG. 10;

FIG. 12B is a rear view of the component of FIG. 12A;

FIG. 13A is a perspective side view of a component of the embodiment of FIG. 10;

FIG. 13B is a top view of the component of FIG. 13A;

FIG. 16A is a perspective side view of a component of the embodiment of FIG. 10;

FIG. 16B is a front view of the component of FIG. 16A;

FIG. 17 is a perspective side view of a tool for use with the embodiment of FIG. 10;

FIG. 18A is a cross-section taken along line 18-18 of FIG. 10;

FIG. 18B is a cross-section taken along line 18-18 of FIG. 10 depicting an alternate configuration;

FIGS. 21A-21D are schematic front views depicting a sequence of operation of the embodiment of FIG. 10.

DESCRIPTION OF EMBODIMENTS

Figure 4:
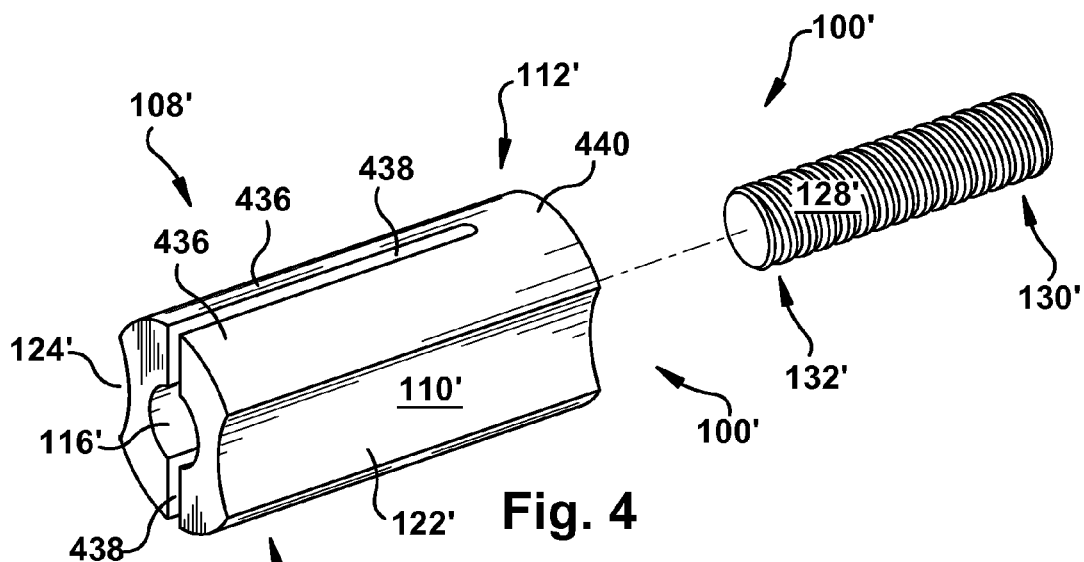
FIG. 4 is an exploded schematic view of an embodiment of the present invention.

In accordance with a first embodiment of the present invention, FIGS. 1A, 1B, 1C, 2A, 2B, 2C, 3A, 3B, and 3C schematically depict an apparatus 100 for anchoring at least two graft ligaments 102 and 104 within a longitudinal bone tunnel 106. More specifically, the apparatus 100 can be a sequentially-actuated graft anchor system 100 for use in anchoring at least two longitudinally extending graft ligaments 102 and 104 within a bone tunnel 106 during replacement of a native anterior cruciate ligament ("ACL"), and will be discussed as such herein. However, one of ordinary skill in the art will recognize that the apparatus 100 may be useful for sequentially anchoring any plurality of elongate strands within an aperture. For example, the apparatus 100 may be used to anchor a plurality of longitudinally extending graft ligaments within a bone tunnel during replacement of a native posterior cruciate ligament.

A longitudinal sleeve 108 has a sleeve outer surface 110 and longitudinally separated proximal and distal sleeve ends 112 and 114, respectively. (Element numbers are omitted from several of FIGS. 1A, 1B, 1C, 2A, 2B, 2C, 3A, 3B, and 3C for clarity of depiction.) A sleeve inner lumen 116 extends between the proximal and distal sleeve ends 112 and 114. The sleeve 108 defines a longitudinal axis 118. The sleeve 108 is adapted for longitudinal placement within the bone tunnel 106 with at least a portion of the at least two graft ligaments 102 and 104 located laterally (as shown by lateral direction arrow 120) between the sleeve outer surface 110 and the bone tunnel 106. The term "lateral" is used herein to reference a direction substantially perpendicular to the longitudinal axis 118.

Optionally, and as shown in FIGS. 1A, 2A, and 3A, the sleeve 108 may include at least two radially spaced ligament-contacting surfaces, with first and second ligament-contacting surfaces 122 and 124, respectively, being spaced radially apart as shown by radial direction arrow 126. The term "radial" is used herein to reference a direction concentric to the longitudinal axis 118. The first and second ligament-contacting surfaces 122 and 124, when present, may be located on the sleeve 108 in lateral opposition to the sleeve inner lumen 116. The first and second ligament-contacting surfaces 122 and 124 may include texturization (e.g., grooves or dappling), adhesives, guide structures, different materials from other portions of the sleeve 108, or otherwise may be differentiated from remaining portions of the sleeve outer surface 110. In the depicted embodiment of FIGS. 1A, 2A, and 3A, each graft ligament 102 and 104 is positioned laterally adjacent a different one of the first and second ligament-contacting surfaces 122 and 124. The graft ligaments 102 and 104 thus are at least partially located between the bone tunnel 106 and the sleeve 108 when the sleeve is at least partially inserted into the bone tunnel 106. Regardless of whether a defined ligament-contacting surface is defined on a particularly discussed sleeve 108 herein, however, at least a portion of the sleeve outer surface 110 will be operative as described to contact the graft ligaments 102 and 104 as desired.

As shown in FIGS. 1B, 1C, 2B, 2C, 3B, and 3C, an actuating member 128 may be provided, the actuating member having longitudinally separated proximal and distal actuating member ends 130 and 132, respectively, and an actuating member outer surface 134. At least a portion of the actuating member may be adapted for selective longitudinal insertion into the sleeve inner lumen 116. At least one of the sleeve 108 and the actuating member 128 may have a cross-sectional footprint that is substantially at least one of circular, elliptical, curvilinear, and linear. The term "cross-sectional footprint" is used herein to indicate a silhouette or projection of all or a portion of the indicated structure, as taken in an orientation perpendicular to the longitudinal axis 118. FIGS. 1D, 1E, 1F, 1G, and 1H depict the apparatus 100 of FIG. 1A in three-dimensional form, with each of these Figures taken from a different vantage point.

Figure 5:
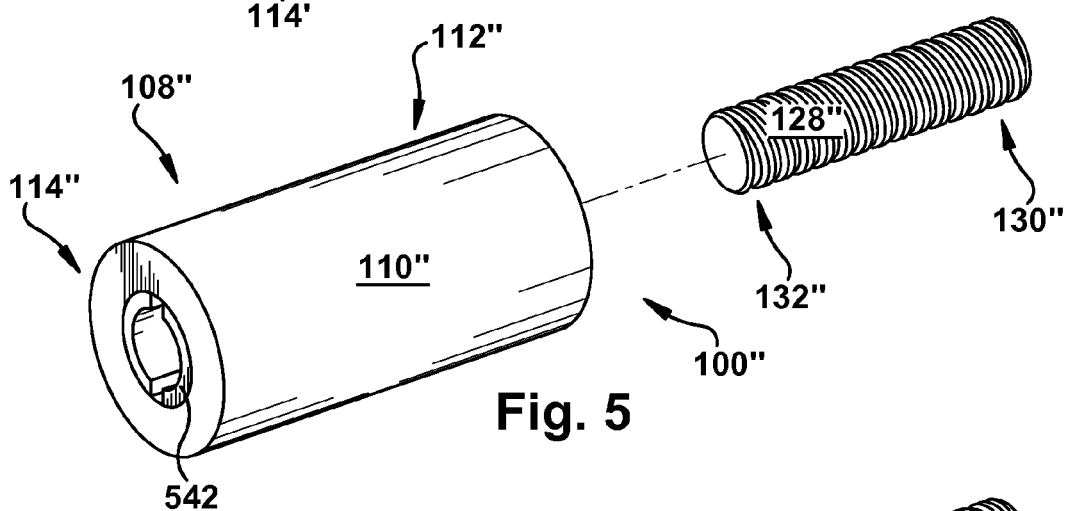
FIG. 5 is an exploded schematic view of an embodiment of the present invention.
Figure 6:
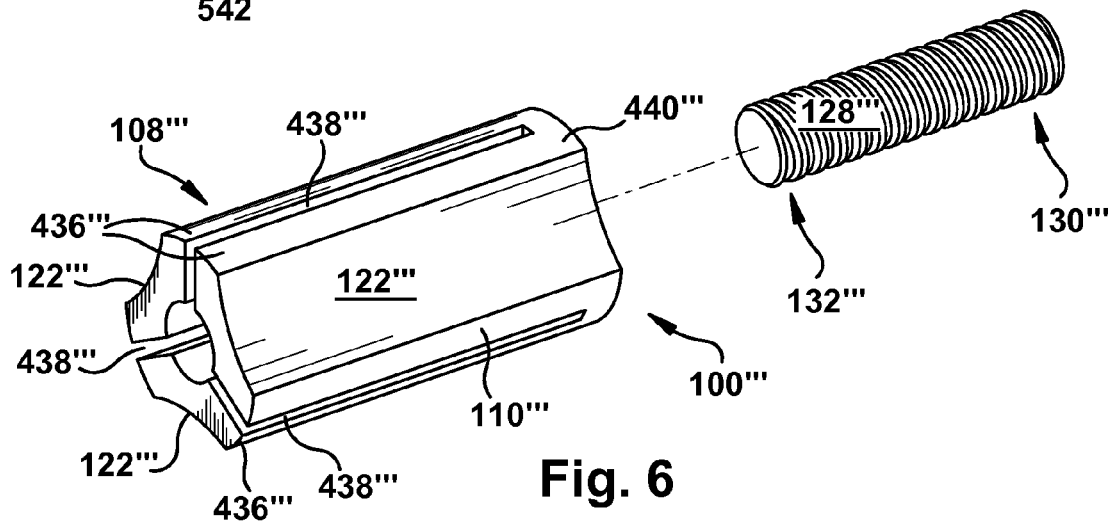
FIG. 6 is an exploded schematic view of an embodiment of the present invention.

FIGS. 4-6 depict exploded schematic views of several optional configurations of sleeve 108 and actuating member 128 pairs which could be used with the apparatus 100. For example, the sleeve 108' of FIG. 4 includes a plurality of longitudinally extending sleeve segment members 436, with each sleeve segment member including a portion of the sleeve outer surface 110' and defining a portion of the sleeve inner lumen 116'. Each of the sleeve segment members 436 can be configured to selectively frictionally engage a different graft ligament (not shown). This frictional engagement is optionally accomplished through the use of first and second ligament-contacting surfaces 122' and 124', which are laterally spaced from the sleeve inner lumen 116'. In the sleeve 108' of FIG. 4, the plurality of sleeve segment members 436 are spaced radially apart by at least one longitudinal aperture 438, and each of the sleeve segment members is connected to a sleeve aggregating member 440, here located at the proximal sleeve end 112', to form the sleeve 108'. As shown, the sleeve segment members 436 are formed integrally with the sleeve aggregating member 440, but the sleeve 108' could instead be constructed in any suitable manner from separately provided components. In use, the sleeve segment members 436 can flex relative to one another under proximal constraint by the sleeve aggregating member 440, the utility of which will become apparent below.

Optionally, the longitudinal apertures 438 may be at least partially filled with a flexible, resilient, elastically deformable, compressible, and/or expandable material to form an expansion joint (not shown). When a material is provided to connect adjacent sleeve segment members 436 and bridge across at least a portion of the intervening longitudinal aperture 438 via an expansion joint arrangement, the sleeve aggregating member 440 may be omitted from the sleeve 108' as being unnecessary to hold the sleeve segment members together.

The sleeve 108" of FIG. 5 is an example of a style which does not have specific ligament-contacting surfaces (though such could be provided in an alternate embodiment, not shown, of the sleeve of FIG. 5). Instead, because at least a portion of the outer sleeve surface 110" reflects the shape of the bone tunnel (not shown, but presumed here to be cylindrical), the graft ligaments may be placed in any relationship to the outer sleeve surface 110" which will facilitate the desired anchoring. In the embodiment of FIG. 5, the outer sleeve surface 110" is configured to provide a cylindrical aspect to the sleeve 108" corresponding to that of the presumed bone tunnel. Because the depicted sleeve 108" does not include longitudinal apertures or other means for facilitating lateral expansion, the sleeve of FIG. 5 may be made of a flexible and optionally resilient, compressible, and/or elastically deformable material, such as, but not limited to, a rubber or plastic material of any suitable type. Optionally, an inner lumen liner 542 of a more-rigid material may be provided to facilitate transfer of forces between the actuating member 128" and the outer sleeve surface 110", as discussed below.

FIG. 6 depicts a sleeve 108''' which is similar to that of FIG. 4 but includes an additional sleeve segment member 436'''. In the FIG. 6 embodiment, the structure and function are similar to those described for the FIG. 4 embodiment, which will not be repeated here, but three ligament contacting surfaces (all labeled 122''' for clarity) are available for use. Any number of the ligament-contacting surfaces can be used to anchor a suitable number of graft ligaments in the manner described below, and the number of ligament-contacting surfaces for any embodiment of the present invention is not necessarily equal to the number of graft ligaments being anchored.

While FIGS. 4-6 depict examples of apparatuses 100', 100", and 100''' which include various combinations of features and structures, there is no limit placed on the number, type, structure, or any other characteristics of the elements which may be combined for use in the present invention. Additionally, each ligament-contacting surface in any embodiment of the present invention may be used to anchor zero, one, or more than one graft ligament during use of that embodiment.

With reference once again, to FIGS. 1A, 1B, 1C, 2A, 2B, 2C, 3A, 3B, and 3C, and regardless of the specific structure or design of the apparatus 100, a sleeve thickness 144 may be defined between the sleeve outer surface 110 and the sleeve inner lumen 116. The sleeve thickness 144 corresponds to a laterally measured amount of sleeve 108 material and may be taken at any point radially around the circumference of the sleeve or longitudinally along the length of the sleeve. Each graft ligament 122 and 124 may be located laterally adjacent at least a portion of a graft ligament position 146 defined on the sleeve outer surface 110, with the graft ligament positions 146 being optionally associated with one or more ligament-contacting surfaces 122 and 124, when present. The sleeve thickness 144 may be a minimum sleeve thickness (disregarding any longitudinal apertures or other localized voids on the sleeve 108) at the graft ligament positions 146. The sleeve thickness 144 may also or instead be a maximum sleeve thickness at a location substantially radially equidistant from each of the graft ligament positions 146. Thus, the sleeve thickness 144 may be used by one of ordinary skill in the art as a tool to quantify and design a sleeve 108 having desired thickness properties for a particular application of the present invention.

At least one of the sleeve 108 and the actuating member 128 may define an asymmetrically offset profile, the asymmetrically offset profile being located at the sleeve-actuating member interface and having a plurality of longitudinally spaced engagement thresholds. The phrase "asymmetrically offset" is used herein to indicate an arrangement wherein a plurality of abrupt changes in the profile of the "offset" structure are located on opposite sides of a dividing line or median plane, or about a center or axis, without a correspondence in relative position. For example, and returning to FIGS. 1A, 1B, 1C, 2A, 2B, 2C, 3A, 3B, and 3C, at least one of the sleeve inner lumen 116 and the actuating member outer surface 134 may define the asymmetrically offset profile in the longitudinal direction, with the asymmetrically offset profile having longitudinally spaced first and second engagement thresholds 148 and 150, respectively. It is contemplated that the asymmetrically offset profile is not necessarily asymmetrical in every conceivable orientation, but that the asymmetry in a particular orientation of interest, such as those shown in the Figures, is sufficient to create the effects and functions described herein.

As is shown in at least FIGS. 1C, 2C, and 3C, the asymmetrically offset profile may include at least one shoulder (two shoulders 152 and 154 shown) defining at least one of the first and second engagement thresholds 148 and 150. The shoulder(s) 152 and 154, when present, are located on a chosen one of the sleeve inner lumen 116 and the actuating member outer surface 134. The shoulder(s) 152 and 154 then interact with the other one of the sleeve inner lumen 116 and the actuating member outer surface 134 to move the sleeve outer surface 110 laterally outward and into frictional engagement with at least one graft ligament 102 and 104. This interaction is prompted and/or caused by relative movement of the actuating member 128 and the sleeve 108, as discussed in detail below. The shoulder(s) 152 and 154 may be angular, curved, curvilinear, or any other shape and may be formed on the chosen one of the sleeve inner lumen 116 and the actuating member outer surface 134 in any suitable manner.

The embodiment of the present invention shown in FIGS. 1A-3C has an asymmetrically offset profile defined by the sleeve inner lumen 116. The first engagement threshold 148 is defined by a first shoulder 152 extending laterally inward toward the longitudinal axis 118 at a first radial location, and the second engagement threshold 150 is defined by a second shoulder 154 extending laterally inward toward the longitudinal axis, optionally at a second radial location. The second radial location, when present, is longitudinally and radially spaced from the first radial location, as is readily apparent from at least FIG. 1C. Optionally, and as is the case with the embodiment of FIGS. 1A-3C, the second radial location may be located radially opposite the first radial location about a circumference of the sleeve 108. However, the first and second radial locations will generally bear a direct relationship to the desired placement of the graft ligaments 102 and 104 about a circumference (when curvilinear) or other inner perimeter shape of the bone tunnel 106. It is contemplated that additional shoulders (not shown) corresponding to additional engagement thresholds (not shown) may be present when more than two graft ligaments are to be anchored, and, depending upon the planned securement, the second shoulder 154 could serve to reinforce the anchoring provided by the first shoulder 152. For example, and as shown in FIG. 1E, the second shoulder 154 could extend around a substantial portion of the sleeve inner lumen 116. One of ordinary skill in the art can readily provide an asymmetrically offset profile to at least one of the sleeve inner lumen 116 and actuating member outer surface 134 which will anchor the graft ligaments in the desired sequence.

The sleeve 108 depicted in FIGS. 1A-3C is an elastomeric or otherwise at least partially resilient sleeve which allows the material of the sleeve to be compressed by the actuating member 128 such that the sleeve expands laterally to frictionally engage the graft ligaments 102 and 104 without a corresponding lateral contraction elsewhere around the sleeve circumference (especially shown in FIGS. 1A, 2A, and 3A). However, the sleeve 108, actuating member 128, or any other structures of the present invention could be made of any suitable material or combination of material having desired properties for a particular application of the present invention.

Optionally, and as discussed above with reference to FIG. 5, a one-piece or multiple-piece inner lumen liner (not shown in FIG. 1A 3C) may be located in the sleeve inner lumen 116 to facilitate force transfer between the actuating member 128 and sleeve 108.

In the embodiment of FIGS. 1A-3C, a substantially straight-sided actuating member 128 interacts with an asymmetrically offset profile on the sleeve inner lumen 116. In contrast, FIGS. 7A-9B schematically depict an apparatus 100b according to a second embodiment of the present invention.

Figure 7A:
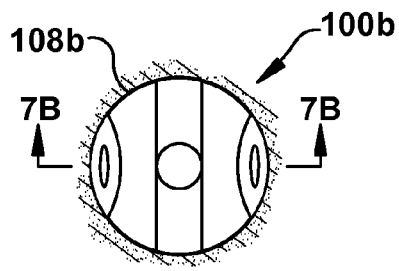
FIG. 7A is a schematic top view of an embodiment of the present invention in a first condition.
Figure 7B:
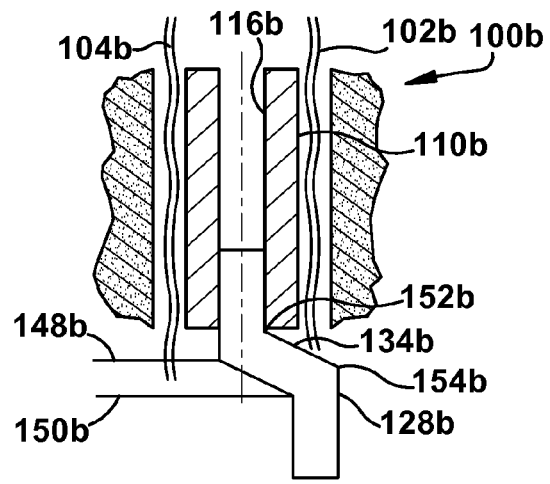
FIG. 7B is a cross-section taken along line 7B-7B of FIG. 7A.
Figure 8A:
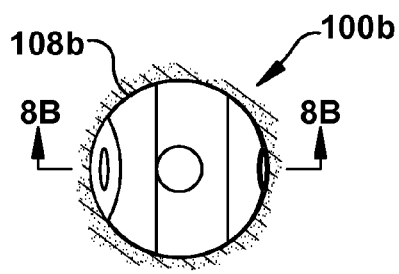
FIG. 8A is a schematic top view of the embodiment of FIG. 7A in a second condition.
Figure 8B:
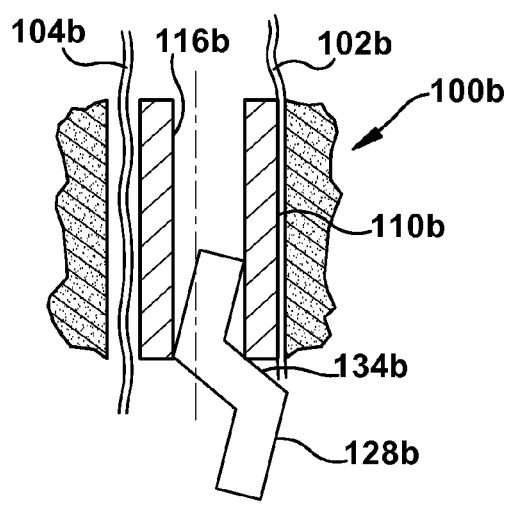
FIG. 8B is a cross-section taken along line 8B-8B of FIG. 8A.
Figure 9A:
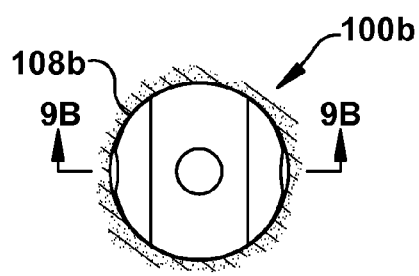
FIG. 9A is a schematic top view of the embodiment of FIG. 7A in a third condition.
Figure 9B:
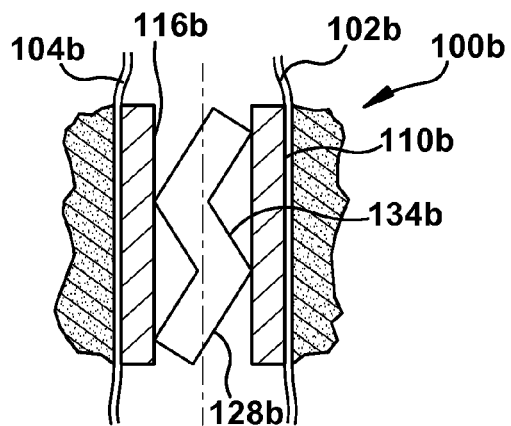
FIG. 9B is a cross-section taken along line 9B-9B of FIG. 9A.

The apparatus 100b of FIGS. 7A-9B is similar to the apparatus 100 of FIGS. 1A-3C and therefore, structures of FIGS. 7A-9B that are the same as or similar to those described with reference to FIGS. 1A-3C have the same reference numbers with the addition of the suffix "a". Description of common elements and operation similar to those in the previously described first embodiment will not be repeated with respect to the second embodiment. In the embodiment of FIGS. 7A-9B, the sleeve 108 is more rigid than in the previously described embodiment and the asymmetrically offset profile is on the actuating member outer surface 134b. Accordingly, the first and second engagement thresholds 148b and 150b are defined by first and second shoulders 152b and 154b on the actuating member 128b. Interaction between the actuating member 128b and the sleeve 108 pushes the sleeve outer surface 110b laterally outward and into frictional engagement with the graft ligaments 102b and 104b in a similar manner to that described below with reference to the first embodiment. While the sleeve 108 in the top views of FIGS. 7A, 8A, and 9A is depicted as having a lateral gap between two opposed ligament-contacting sides, it is contemplated that a flexible sheath, sleeve aggregating member, or other unifying structure (not shown) could be provided to facilitate handling and installation of the depicted sleeve.

The first embodiment of FIGS. 1A-3C is used here to illustrate a described method of anchoring at least two longitudinally extending graft ligaments 102 and 104 within a bone tunnel 106, with replacement of a native ACL being the example application for the method. To prepare for the anchoring and bring the apparatus 100 into the arrangement of FIGS. 1A-1C, the first graft ligament 102 is extended longitudinally through the bone tunnel 106, and the second graft ligament 104 is extended longitudinally through the bone tunnel at a location radially spaced from the first graft ligament. The sleeve 108 is placed longitudinally within the bone tunnel 106 with at least a portion of each of the first and second graft ligaments 102 and 104 being located laterally between the sleeve outer surface 110 and the bone tunnel. Optionally, the first and second graft ligaments 102 and 104 may respectively be located laterally between first and second ligament-contacting surfaces 122 and 124 and the bone tunnel 106.

Once the graft ligaments 102 and 104 and sleeve 108 are arranged within the bone tunnel 106, at least a portion of the actuating member 128 is longitudinally inserted into the sleeve inner lumen 116. The actuating member 128 is then advanced distally into the sleeve inner lumen 116, with respect to the sleeve 108, in any suitable manner. For example, the actuating member 128 may threadably engage with the sleeve inner lumen 116, as shown in FIGS. 1A-3C, to produce the claimed distal advancement of the actuating member into the sleeve inner lumen. As another example, the actuating member 128b may slidably engage with the sleeve inner lumen 116b, as shown in FIGS. 7A-9B, to produce the claimed distal advancement.

Regardless of the way in which the actuating member 128 is advanced distally into the sleeve inner lumen 116, the user applies a first predetermined force, which will normally be a tensile force, to the first graft ligament 102 before anchoring. In an ACL replacement procedure, this force may correspond to the force exerted on/by the first bundle of a native ACL. Once the first graft ligament 102 has been adjusted as desired, the actuating member 128 is advanced distally across the first engagement threshold 148 to cause the first graft ligament to frictionally engage the sleeve outer surface 110 and the bone tunnel 106. More particularly, in the embodiment of FIGS. 1A-3C, as the actuating member 128 reaches the first engagement threshold 148, at least a portion of both the actuating member and the sleeve 108 become laterally adjacent to the first engagement threshold 148. In this arrangement, the distal actuating member end 132 presses against the first shoulder 152 and thus presses at least a local portion of the sleeve 108 outward to engage the first graft ligament 102 as described. At this point the apparatus 100 is in substantially the position depicted schematically in FIGS. 2A-2C, with the first graft ligament 102 anchored.

The actuating member 128 is then advanced further distally in any suitable manner and the body of the actuating member partially blocks the sleeve inner lumen 116 and thus prevents the laterally expanded portion of the sleeve 108 (i.e., the portion pressed laterally outward toward the first graft ligament 102) from reverting to an original position. At any time before, during, or after the first graft ligament 102 is anchored, the user applies a second predetermined force, which will normally be a tensile force, to the second graft ligament 104 before anchoring. In an ACL replacement procedure, this force may correspond to the force exerted on/by the second bundle of a native ACL. Once the second graft ligament 104 has been adjusted as desired, the actuating member 128 is advanced distally across the second engagement threshold 150 to cause the second graft ligament to frictionally engage the sleeve outer surface 110 and the bone tunnel 106. More particularly, in the embodiment of FIGS. 1A-3C, as the actuating member 128 reaches the second engagement threshold 150, at least a portion of both the actuating member and the sleeve 108 become laterally adjacent to the second engagement threshold 150. In this arrangement, the distal actuating member end 132 presses against the second shoulder 154 and thus presses at least a local portion of the sleeve 108 outward to engage the second graft ligament 104 as described. At this point the apparatus 100 is in substantially the position depicted schematically in FIGS. 3A-3C, with the first and second graft ligaments 102 and 104 anchored.

It should be noted that the frictional engagement of each of the first and second graft ligaments 102 and 104, and indeed of any other provided graft ligaments (not shown), with both the bone tunnel 106 and the sleeve 108 (optionally at a ligament-contacting surface) is temporally spaced apart from the frictional engagement of at least one other graft ligament with the bone tunnel 106 and the sleeve 108. This temporal spacing is provided by the engagement thresholds associated with each of the graft ligaments, and can be controlled by one of ordinary skill in the art through placement and design of the engagement thresholds.

Optionally, and as shown in FIGS. 1A-3C, the actuating member 128 may advance substantially laterally symmetrically along the longitudinal axis 118 concurrently with lateral movement of at least a portion of the sleeve 108 away from the longitudinal axis as the actuating member crosses the first and second engagement thresholds 148 and 150 while traveling in the distal direction. In other words, the actuating member 128 is advanced (e.g., via the threaded engagement of FIGS. 1A-3C) in a manner which appears linear from the frame of reference of the bone tunnel and pushes various portions of the sleeve 108 successively outward through engagement of the distal actuating member end 132 with the first and second shoulders 152 and 154. This situation is most likely to occur when the asymmetrically offset profile is on the sleeve inner lumen 116, as opposed to the actuating member outer surface 134, and may be facilitated by the choice of a sleeve 108 material which has the desired rigidity and compressibility properties to accomplish the anchoring in a suitable manner.

While the above description uses the first embodiment of FIG. 1A 3C as an example, one of ordinary skill in the art can readily translate the described events to an embodiment, such as the second embodiment shown in FIGS. 7A-9B, having the asymmetrically offset profile located on the actuating member 128. In this latter configuration, the temporal spacing of the anchoring of the first and second graft members 102 and 104 is also provided by the engagement thresholds; the engagement thresholds are merely located on a different portion of the apparatus 100 than in the first embodiment of FIGS. 1A-3C.

In configurations of the sleeve 108 including sleeve segment members 436, such as those of FIGS. 4 and 6, the first and second (and any additionally provided) shoulders 152 and 154 may each be associated with a sleeve segment member. During deployment of apparatuses having these or similar configurations, the actuating member 128 may flex the sleeve segment members 436 outward and into frictional engagement with associated graft ligaments 102 and 104 through pressure of the distal actuating member end 132 on the first and second shoulders 152 and 154.

Though the above description refers to the sleeve 108 as being "expanded" into contact with the first and second graft ligaments 102 and 104, one of ordinary skill in the art will recognize that various radially spaced portions of the sleeve may be laterally moved and/or shifted into engagement with the first and second graft ligaments and/or the bone tunnel in various ways, depending upon the material and structure of the sleeve, and the interrelations of the asymmetrically offset profile with the other portions of the apparatus 100. The sleeve 108 may be a unitary piece or may be formed of separate component parts. One of ordinary skill in the art will also be readily able to provide an elastically or plastically deformable sleeve 108 and control the interaction of various portions of the apparatus 100 to anchor the first and second graft ligaments 102 and 104 accordingly.

Figure 10:
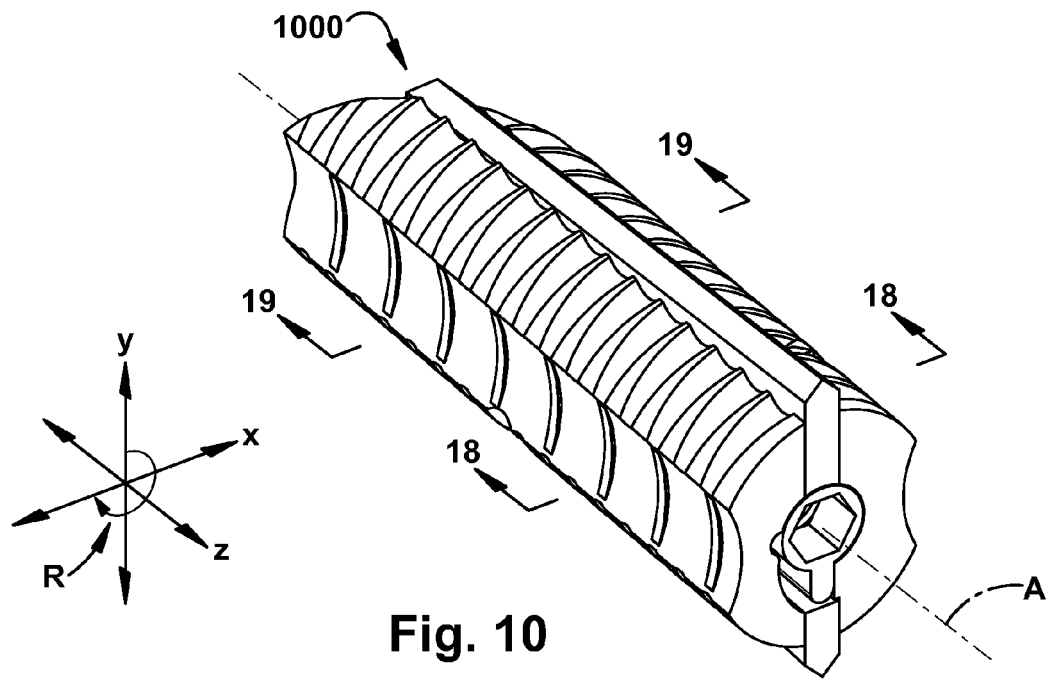
FIG. 10 is a perspective side view of an embodiment of the present invention.
Figure 11:
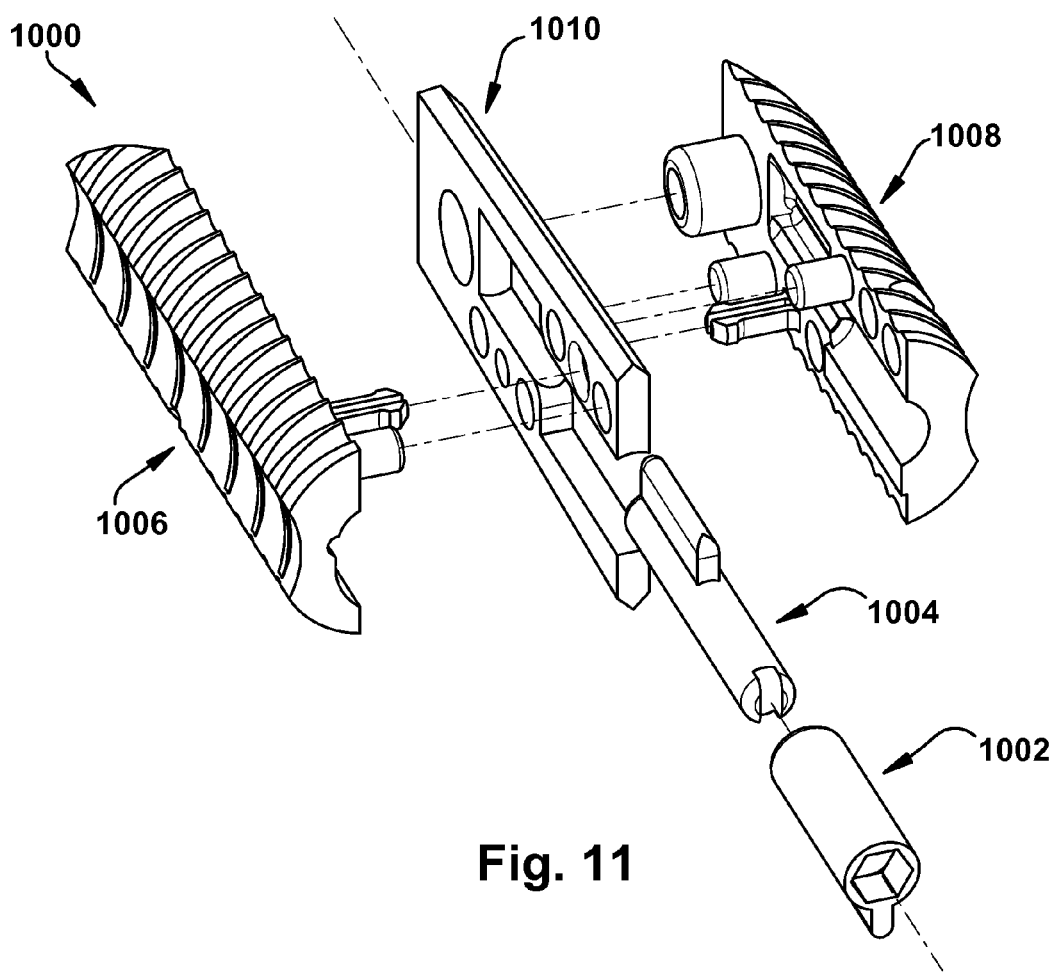
FIG. 11 is an exploded view of the embodiment of FIG. 10.

In accordance with a third embodiment of the present invention, FIGS. 10 and 11 schematically depict an anchoring apparatus 1000 for anchoring at least two elongate strands (omitted from FIGS. 10 and 11) within a longitudinal bone tunnel (omitted from FIGS. 10 and 11). Specifically, the anchoring apparatus 1000 is configured for anchoring the first and second elongate strands against a longitudinal bone tunnel wall (omitted from FIGS. 10 and 11) of the bone tunnel. More specifically, the anchoring apparatus 1000 may be a sequentially-actuated graft anchor apparatus 1000 for use in anchoring at least two longitudinally extending graft ligaments within a bone tunnel during replacement of a native anterior cruciate ligament ("ACL"), and will be discussed as such herein. Description of common elements and operation similar to those in the previously described embodiments will not be repeated, for clarity, with respect to the anchoring apparatus 1000.

Since directions and orientations are used throughout the description of the anchoring apparatus 1000, a three-dimensional coordinate system has been placed in FIG. 10 to clarify the references made herein. The "longitudinal" direction, as referenced herein, substantially corresponds to the Z-axis shown in FIG. 1. A direction "lateral" to the Z-axis will lie substantially in a plane defined by the X- and Y-axes shown in FIG. 1. In reference to the anchoring apparatus 1000, a longitudinal axis A of the anchoring apparatus 1000 can substantially extend longitudinally (i.e., substantially parallel to the Z-axis) therethrough. The term "radial" is used with reference to FIG. 10 and the third embodiment of the present invention to reference a rotary direction R that is substantially concentric about the Z-axis, but one of ordinary skill in the art will understand that a "radial" direction may be defined with respect to any other axis, named or unnamed, as appropriate to aid in describing a particular rotary direction.

One of ordinary skill in the art will recognize that the anchoring apparatus 1000 may be useful for sequentially anchoring any plurality of elongate strands within an aperture. For example, the anchoring apparatus 1000 may be used during various surgical procedures including, but not limited to, posterior cruciate ligament ("PCL") repairs, abductor tendon repairs, posterior capsular repairs of the hip, Achilles' tendon repairs, patellar tendon repairs, quadriceps tendon repairs, shoulder biceps tenodesis, knee extra articular reconstructions, ankle ligament reconstructions, elbow ligament reconstructions, expandable interbody device implantations, Posterior Lumbar Interbody Fusion ("PLIF") implantations, Transforaminal Lumbar Interbody Fusion ("TLIF") implantations, Anterior Lumbar Interbody Fusion ("ALIF") implantations, Lateral Lumbar Interbody Fusion ("LLIF") implantations, Cervical Interbody implantations, Corpectomy Devices implantations, and Laminoplasty Stabilization Device implantations, and other appropriate surgical procedures.

One of ordinary skill in the art will also recognize that the anchoring apparatus 1000, as with any embodiment of the present invention, may be used with any type of rigid or at least partially flexible elongate strand, such as, but not limited to, ligaments, tendons, sutures, threads, wires, fibers, filaments, yarns, ropes, strips, tapes, or the like. The elongate strands used with the present invention made out of any suitable material or combinations of materials such as, but not limited to, natural or artificial tissues, plastics, fabrics, metals, or the like. An "elongate strand" is used herein to reference any structure which has a longitudinal length which is significantly larger than a size of the elongate strand in a direction which is substantially perpendicular to the longitudinal direction.

In one example embodiment, the anchoring apparatus 1000 may include first and second cams 1002 and 1004 operatively connected to first and second anchor members 1006 and 1008, respectively. The first cam 1002 may be rotated to cause the first anchor member 1006 to move laterally (i.e., along the X-Y plane) away from the longitudinal axis A and thereby frictionally engage at least one elongate strand to urge the at least one elongate strand against a tunnel wall. The second cam 1004 may be rotated before, during, and/or after lateral movement of the first anchor member 1006 to cause a second anchor member 1008 to move laterally away from the longitudinal axis A and thereby frictionally engage at least one elongate strand to urge the at least one elongate strand against the tunnel wall.

As shown in FIG. 11, the anchoring apparatus 1000 includes the first cam 1002, the second cam 1004, the first anchor member 1006, the second anchor member 1008, and a support member 1010. The first and second cams 1002 and 1004 are configured for attachment to the support member 1010, and are also configured for engagement with the corresponding first and second anchor members 1006 and 1008, as described in more detail below.

FIGS. 12A and 12B show an embodiment of the first cam 1002 that is configured to apply a force to the first anchor member 1006 to cause lateral movement of the first anchor member 1006. The first cam 1002 has a main first cam body 1012. The main first cam body 1012 may have a generally cylindrical shape (or have any other desired shape) as shown in FIG. 12A. The main first cam body 1012 may be made of a hard plastic (e.g., polyurethane, or the like), a soft plastic (e.g., polyethylene, or the like), a metal (e.g., aluminum, or the like), or any other suitable material (e.g., a ceramic) or combination of materials. The main first cam body 1012 has a rigid or a semi-rigid configuration to assist with selectively applying a force to the first anchor member 1006.

The main first cam body 1012 includes an outer first cam surface 1014 and an inner first cam surface 1016. The main first cam body 1012 also includes a proximal first cam surface 1018 longitudinally spaced from a distal first cam surface 1020. The proximal and distal first cam surfaces 1018 and 1020 extend laterally between the outer and inner first cam surfaces 1014 and 1016.

The inner first cam surface 1016 defines a longitudinally oriented first cam driver-engaging feature 1022 that extends at least partially longitudinally between the proximal and distal first cam surfaces 1018 and 1020. The first cam driver-engaging feature 1022 is disposed adjacent the proximal first cam surface 1018 and is spaced from the distal first cam surface 1020. As shown in FIG. 12A, the first cam driver-engaging feature 1022 is shown as a female member having a hexagonal cross-section. It will be appreciated that the first cam driver-engaging feature 1022 may have any other suitable configuration (e.g., a male member) or having any desired cross-sectional shape (e.g., rectangular, square, triangular, clutch, an Allen wrench recess, a Philips screwdriver recess, a square Philips screwdriver recess a slotted screwdriver recess, a TORX™ wrench recess, a Robertson wrench recess, an outside hex wrench recess, an inside hex wrench recess, or the like).

The first cam driver-engaging feature 1022 includes a proximal first cam driver-engaging feature end 1024 and a distal first cam driver-engaging feature end 1026 longitudinally spaced from the proximal first cam driver-engaging feature end 1024. The proximal first cam driver-engaging feature end 1024 is substantially laterally coplanar with the proximal first cam surface 1018. The distal first cam driver-engaging feature end 1026 is interposed longitudinally between the proximal and distal first cam surfaces 1018 and 1020.

The inner first cam surface 1016 may also define a longitudinally oriented first cam-engaging feature 1028 that extends between the proximal and distal first cam surfaces 1018 and 1020. It will be appreciated that the first cam-engaging feature 1028 is so named because it is disposed on at least a portion of the first cam 1002. The first cam-engaging feature 1028 is disposed adjacent the distal first cam surface 1020 and is spaced from the proximal first cam surface 1018. As shown in FIG. 12B, a rear view of the first cam 1002, the first cam-engaging feature 1028 is shown as a female member having a circular cross-section for receiving a portion of the second cam 1004. It will be appreciated that the first cam-engaging feature 1028 may have any other suitable configuration, or any desired cross-sectional shape, for engaging a portion of the second cam 1004 (e.g. a male member).

The first cam-engaging feature 1028 includes a distal first cam-engaging feature end 1030 and a proximal first cam-engaging feature end 1032 longitudinally spaced from the distal first cam-engaging feature end 1030. The distal first cam-engaging feature end 1030 is substantially laterally coplanar with the distal first cam surface 1018. As shown in FIG. 12A, the proximal first cam-engaging feature end 1032 is positioned longitudinally adjacent the distal first cam driver-engaging feature end 1026. It will be appreciated that the proximal first cam-engaging feature end 1032 may be longitudinally spaced from the distal first cam driver-engaging feature end 1026.

The main first cam body 1012 also includes a first cam flange 1034 configured to engage a portion of the first anchor member 1006. The first cam flange 1034 may extend laterally from a portion of the outer first cam surface 1014. The first cam flange 1034 may be made of the same material (or combination of materials) as, or a different material (or combination of materials) than, the main first cam body 1012. As shown in FIG. 12A, the first cam flange 1034 substantially extends along the entire length of the main first cam body 1012 between the proximal and distal first cam surfaces 1018 and 1020. It will be appreciated that the first cam flange 1034 instead could extend along just a portion of the length of the main first cam body 1012.

The first cam flange 1034 includes a first anchor member-contacting surface 1036 extending longitudinally between proximal and distal first cam flange faces 1038 and 1040. It will be appreciated that the first anchor member-contacting surface 1036 is so named because it contacts a portion of the first anchor member 1006. The first anchor member-contacting surface 1036 may have an arcuate cross-sectional shape (or have any other suitable cross-sectional shape). At least one of the proximal and distal first cam flange faces 1038 and 1040 may extend laterally from a portion of the respective proximal and distal first cam surfaces 1018 and 1020. The first anchor member-contacting surface 1036 is configured to contact and apply a motive force to the first anchor member 1006, as described in more detail below.

FIGS. 13A and 13B show an embodiment of the second cam 1004 that is configured to apply a force to the second anchor member 1008 to cause lateral movement of the second anchor member 1008. The second cam 1004 has a main second cam body 1042. The main second cam body 1042 may have a generally cylindrical shape (or have any other desired shape) as shown in FIG. 13A. The main second cam body 1042 may be made of a hard plastic (e.g., polyurethane, or the like), a soft plastic (e.g., polyethylene, or the like), a metal (e.g., aluminum, or the like), or any other suitable material (e.g., a ceramic) or combination of materials. The main second cam body 1042 may have a rigid or a semi-rigid configuration to selectively apply a force to the second anchor member 1008.

The main second cam body 1042 includes an outer second cam surface 1044 and an inner second cam surface 1046. The main second cam body 1042 also includes a proximal second cam surface 1048 longitudinally spaced from a distal second cam surface 1050. It will be appreciated that the inner second cam surface 1046 may extend from the proximal second cam surface 1048 and terminate in a portion of the main second cam body 1042 that is longitudinally spaced distally from the proximal second cam surface 1048. The proximal second cam surface 1048 extends laterally between the outer and inner second cam surfaces 1044 and 1046.

The inner second cam surface 1046 defines a longitudinally-oriented second cam driver-engaging feature 1052 that extends distally longitudinally from the proximal second cam surface 1048. The second cam driver-engaging feature 1052 is disposed adjacent the proximal second cam surface 1048 and is spaced from the distal second cam surface 1050. As shown in FIGS. 13A and 13B, the second cam driver-engaging feature 1052 is shown as a female member having a rectangular-shaped cross-section. It will be appreciated that the second cam driver-engaging feature 1052 may have any other suitable configuration (e.g., as a male member) or any other desired cross-sectional shape (e.g., rectangular, square, triangular, clutch, an Allen wrench recess, a Philips screwdriver recess, a square Philips screwdriver recess a slotted screwdriver recess, a TORX™ wrench recess, a Robertson wrench recess, an outside hex wrench recess, an inside hex wrench recess, or the like).

The second cam driver-engaging feature 1052 includes a distal second cam driver-engaging feature end 1054 and a proximal second cam driver-engaging feature end 1056. The distal second cam driver-engaging feature end 1054 is interposed longitudinally between the proximal and distal second cam surfaces 1048 and 1050. The proximal second cam driver-engaging feature end 1056 is substantially coplanar with the proximal second cam surface 1048.

A portion of the outer second cam surface 1044 also defines a longitudinally oriented second cam-engaging feature 1058 that extends between the proximal and distal second cam surfaces 1048 and 1050. It will be appreciated that the "second cam-engaging feature" is so named because it is disposed on at least a portion of the second cam 1004. The second cam-engaging feature 1058 is disposed adjacent the proximal second cam surface 1048 and is spaced from the distal second cam surface 1050.

As shown in FIGS. 13A and 13B, the second cam-engaging feature 1058 includes a proximal second cam-engaging feature end 1060 and a distal second cam-engaging feature end 1062 longitudinally spaced from the proximal second cam-engaging feature end 1060. The proximal second cam-engaging feature end 1060 is substantially laterally coplanar with the proximal second cam surface 1048. As shown in FIG. 13, the distal second cam-engaging feature end 1062 is longitudinally spaced from both of the proximal and distal second cam surfaces 1048 and 1050. For example, the distal second cam-engaging feature end 1062 may be substantially centrally located on the main second cam body 1042, and may be longitudinally spaced from the distal second cam driver-engaging feature end 1054.

As shown in FIG. 13A, the second cam-engaging feature 1058 may be configured as a male member having a lateral circular cross-sectional shape for engaging at least a portion of the first cam-engaging feature 1028. It will be appreciated that the second cam-engaging feature 1058 may have any other suitable configuration (e.g., a female member) or any other desired cross-sectional shape for engaging at least a portion of the first cam-engaging feature 1028. It will also be appreciated that, as shown in FIG. 13B, the second cam driver-engaging feature 1052 is disposed on the proximal second cam-engaging feature end 1060.

The main second cam body 1042 also includes a second cam flange 1064 configured to engage a portion of the second anchor member 1008. The second cam flange 1064 may extend from a portion of the outer second cam surface 1044. The second cam flange 1064 may be made of the same or a different material (or combination of materials) as the main second cam body 1042. As shown in FIG. 13A, the second cam flange 1064 may extend longitudinally along a portion of the length of the main second cam body 1042 between the proximal and distal second cam surfaces 1048 and 1050. The second cam flange 1064 is positioned adjacent the distal second cam surface 1050, and is longitudinally spaced from the proximal second cam surface 1048. It will be appreciated that the second cam flange 1064 may instead extend across substantially the entire length of the main second cam body 1042 (not shown) such that the second cam flange is also positioned adjacent the proximal second cam surface 1048.

The second cam flange 1064 includes a second anchor member-contacting surface 1066 extending longitudinally between proximal and distal second cam flange faces 1068 and 1070. It will be appreciated that the second anchor member-contacting surface 1066 is so named because it contacts a portion of the second anchor member 1008. The second anchor member-contacting surface 1066 may have an arcuate cross-sectional shape, as shown, or have any other suitable cross-sectional shape. The proximal second cam flange face 1068 may extend laterally from a portion of the distal second cam surface 1050. The proximal second cam flange face 1068 may extend laterally from a portion of the main second cam body 1042.

As shown in FIGS. 13A and 13B, the proximal second cam flange face 1068 is positioned laterally adjacent the distal second cam-engaging feature end 1062. It will be appreciated that the proximal second cam flange face 1068 may be longitudinally spaced from the proximal second cam-engaging feature end 1060. The second anchor member-contacting surface 1066 shown in FIG. 13 extends longitudinally between the proximal and distal second cam flange faces 1068 and 1070. The second anchor member-contacting surface 1066 is configured to contact and apply a motive force to the second anchor member 1008, as described in more detail below.

Figure 14A:
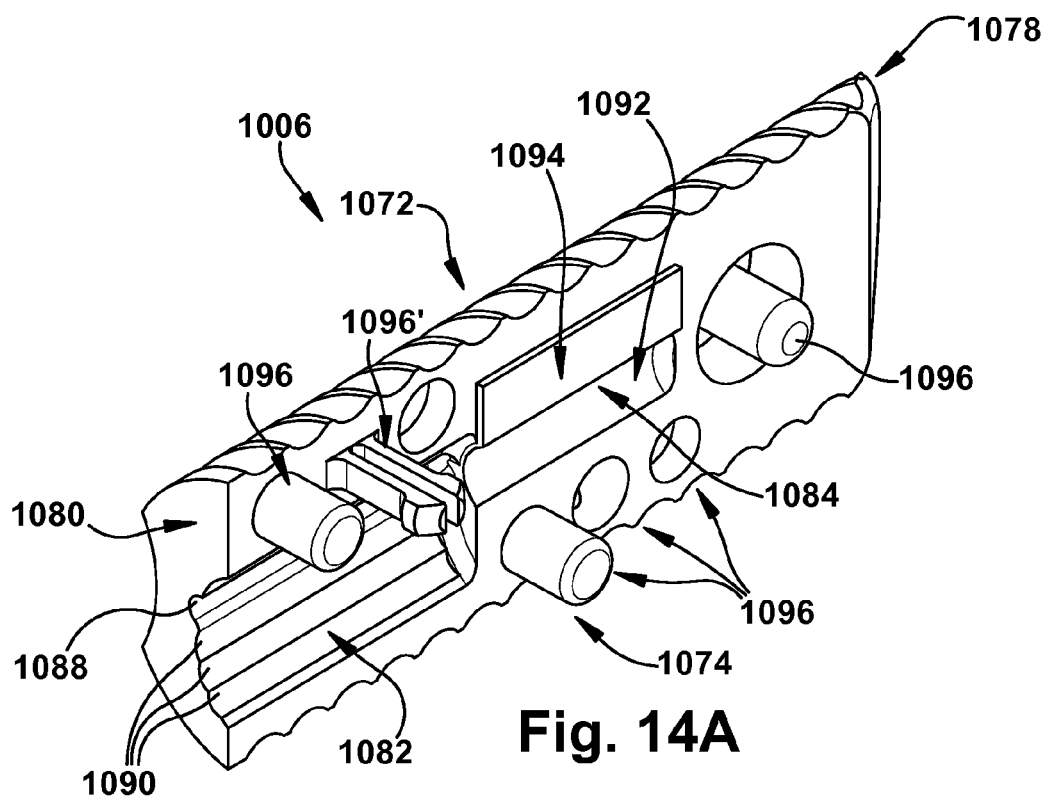
FIGS. 14A and 14B are perspective side views of a component of the embodiment of FIG. 10.
Figure 14B:
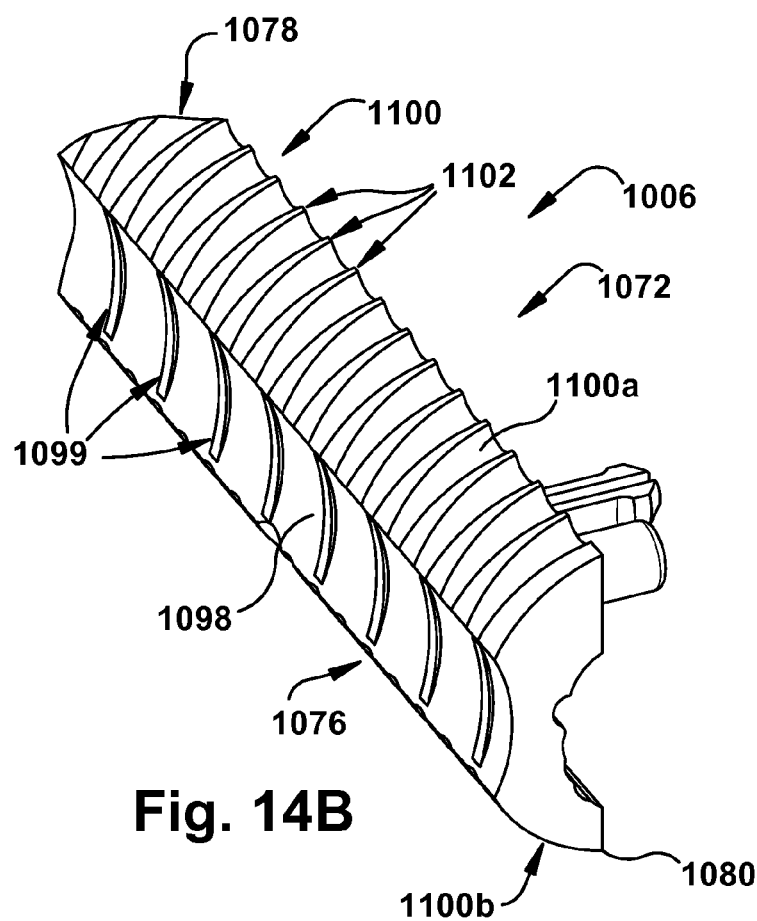

FIGS. 14A and 14B show an embodiment of the first anchor member 1006 configured to anchor at least one elongate strand within a tunnel. The first anchor member 1006 may be configured for engagement with the first cam 1002, as described in more detail below.

The first anchor member 1006 has a main first anchor member body 1072. The main first anchor member body 1072 may have a generally rectangular shape (or have any other desired shape) when viewed in a direction normal to a substantially longitudinally extending surface of the main first anchor member body 1072, such as a first cam-contacting surface 1074. The main first anchor member body 1072 may be made of a hard plastic (e.g., polyurethane, or the like), a soft plastic (e.g., polyethylene, or the like), a metal (e.g., aluminum, or the like), or any other suitable material (e.g., a ceramic) or combination of materials. The main first anchor member body 1072 may have a rigid or a semi-rigid configuration to selectively apply a laterally outwardly-oriented anchoring force to at least one elongate strand, as described in more detail below.

The main first anchor member body 1072 includes the first cam-contacting surface 1074 and a first strand-contacting surface 1076 laterally spaced on the main first anchor member body 1072 substantially opposite the first cam-contacting surface 1074. The main first anchor member body 1072 also includes a distal first anchor member surface 1078 longitudinally spaced from a proximal first anchor member surface 1080. The distal and proximal first anchor member surfaces 1078 and 1080 extend laterally between the first cam-contacting side 1074 and the first strand-contacting side 1076.

The first cam-contacting surface 1074 includes a first cam-receiving portion 1082 configured to selectively receive at least a portion of the first cam 1002, a second cam-receiving portion 1084 configured to selectively receive at least a portion of the second cam 1004, and a support member-contacting surface 1086 configured to selectively contact a portion of the support member 1010.

The first cam-receiving portion 1082 includes a first anchor member stop 1088 that protrudes more deeply into the main first anchor member body 1072 than does the first cam-receiving portion 1082. The first anchor member stop 1088 is configured to engage a portion of the first cam flange 1034, as described in more detail below. The first cam-receiving portion 1082 may also include at least one first anchor member detent 1090 disposed adjacent the first anchor member stop 1088. The at least one first anchor member detent 1090 is configured to at least temporarily engage a portion of the first cam flange 1034. As shown in FIG. 14A, the at least one first anchor member detent 1090 comprises a plurality of first anchor member detents 1090 disposed adjacent each other. It will be appreciated that each first anchor member detent 1090 may be radially spaced from the other first anchor member detents 1090.

The second cam-receiving portion 1084 includes a second cam main body-receiving portion 1092 configured to receive at least a portion of the main second cam body 1042 and a second cam flange-support portion 1094 configured to support at least a portion of the second cam flange 1064. As shown in FIG. 14A, the second cam-receiving portion 1084 may be positioned longitudinally adjacent the first cam-receiving portion 1082. It will be appreciated that the second cam-receiving portion 1084 may instead be longitudinally spaced from the first cam-receiving portion 1082.

The support member-contacting surface 1086 may include at least one first anchor member engagement member 1096, so named because the first anchor member engagement members contact a portion of the support member 1010. The first anchor member engagement members 1096 can be disposed on at least a portion of the support member-contacting surface 1086. The first anchor member engagement members 1096, when present (a plurality of which will be described herein), are each configured to engage a corresponding portion of the second anchor member 1008, as described in more detail below. In one example, at least one of the first anchor member engagement members 1096 may be configured as a male member (e.g., a tab) or a female member (e.g., a recess) disposed on a portion of the first cam-contacting side 1074 and configured to telescopingly engage with a corresponding portion of the second anchor member 1008 to guide relative movement of the first and second anchor members 1006 and 1008. In another example, at least one of the plurality of first anchor member engagement members 1096' may be configured as an elastic tab configured to contract and expand into locking engagement with a corresponding portion of the second anchor member 1008, optionally in a telescoping manner, to prevent undesired lateral movement of the first and second anchor members 1006 and 1008.

The first strand-contacting surface 1076 includes a first strand-contacting portion 1098 configured to selectively contact at least a portion of at least one elongate strand. The first strand-contacting portion 1098 extends longitudinally between the proximal and distal first anchor member surfaces 1078 and 1080. In one example, as shown in FIG. 14B, the first strand-contacting portion 1098 is substantially radially centrally located on the first strand-contacting surface 1076. The first strand-contacting portion 1098 may have any other suitable location (e.g., centrally offset, vertically, etc.) on the first strand-contacting surface 1076. The first strand-contacting portion 1098 has a generally convex profile; however, the first strand-contacting portion 1098 may have a generally planar profile, a generally concave profile, a combination profile, or any other suitable profile.

As shown in FIG. 14B, the first strand-contacting portion 1098 may include a plurality of first anchor member ribs 1099 configured to contact a portion of at least one elongate strand to prevent unwanted longitudinal movement of the at least one elongate strand. The first anchor member ribs 1099 extend laterally along substantially the entire first strand-contacting portion 1098; however, it will be appreciated that the first anchor member ribs 1099 may be present along only a portion of the length of the first strand-contacting portion 1098.

The first strand-contacting surface 1076 also includes a first tunnel wall-contacting portion 1100 configured to selectively engage a portion of a tunnel wall. In one example, when the first strand-contacting portion 1098 is substantially laterally centrally located on the first strand-contacting surface 1076, a pair of first tunnel wall-contacting portions 1100a and 1100b is radially disposed on opposing sides of the first strand-contacting portion 1098. The first tunnel wall-contacting portion 1100 may be radially centrally offset on opposing sides of the first strand-contacting portion 1098. The first tunnel wall-contacting portion 1100 may have any other suitable location (e.g., centrally offset, vertically, etc.) on the first strand-contacting surface 1076.

The first strand-contacting surface 1076 may also include a plurality of first anchor member ridges 1102 configured to contact a portion of a bone tunnel wall, as described in more detail below. The first anchor member ridges 1102 extend laterally along substantially the entire first tunnel wall-contacting portion 1100; however, it will be appreciated that the first anchor member ridges 1102 may be present along only a portion of the length of the main first anchor member body 1072.

Figure 15A:
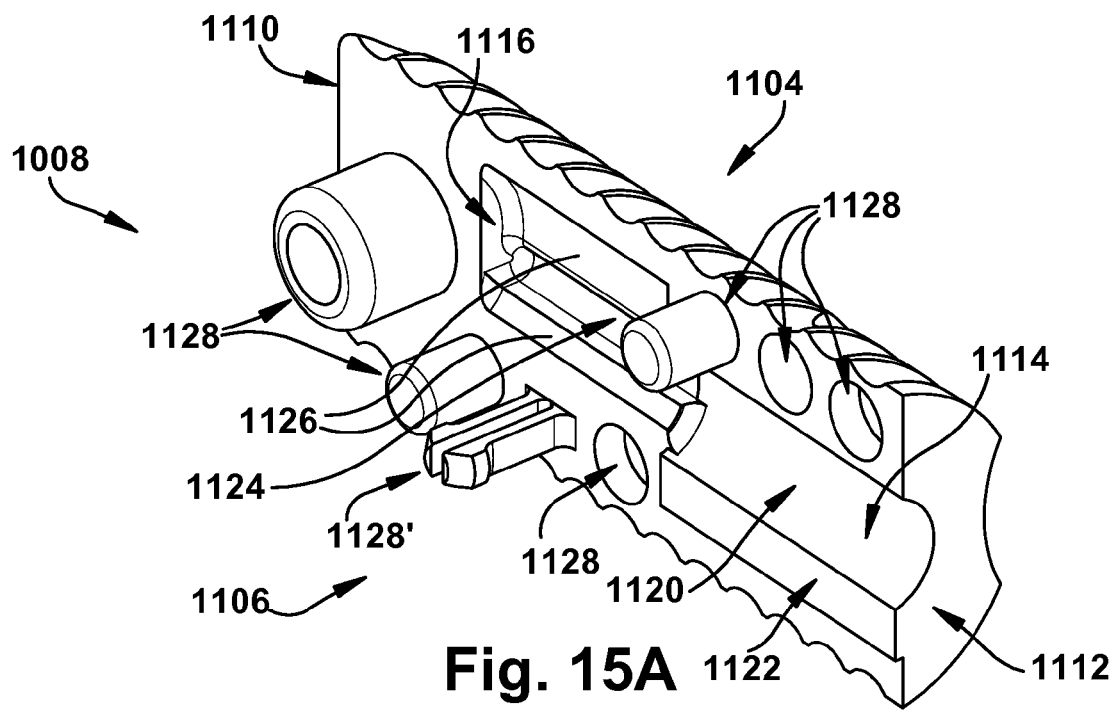
FIGS. 15A and 15B are perspective side views of a component of the embodiment of FIG. 10.
Figure 15B:
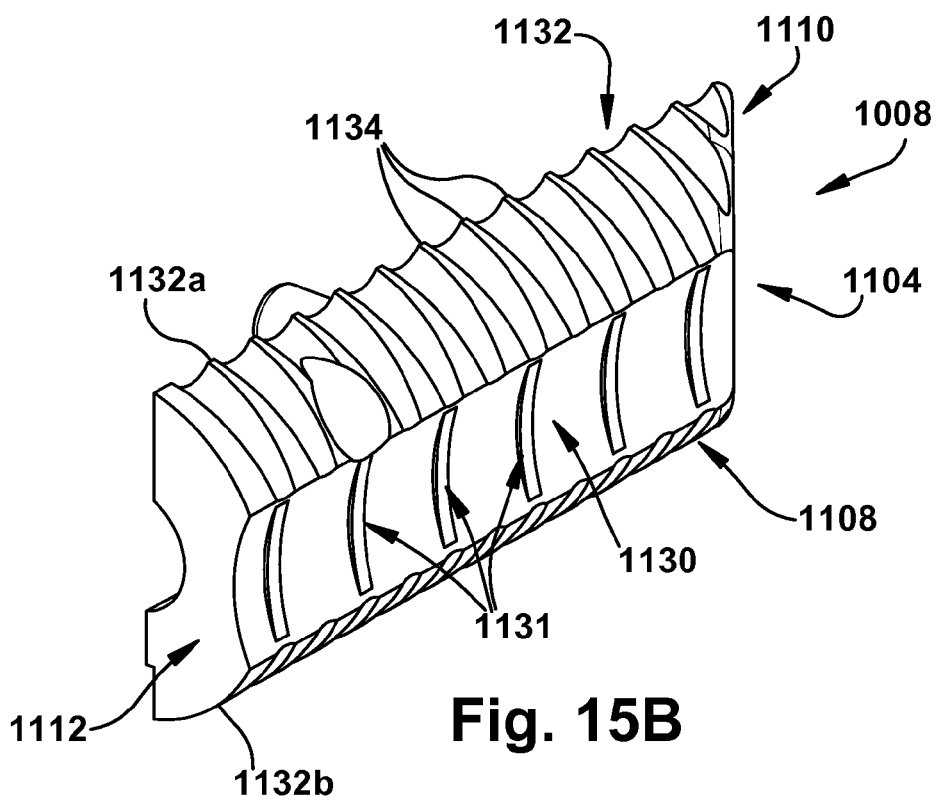

FIGS. 15A and 15B show an embodiment of the second anchor member 1008 configured to anchor at least one elongate strand within a tunnel. The second anchor member 1008 may be configured for engagement with the second cam 1004, as described in more detail below.

The second anchor member 1008 has a main second anchor member body 1104. The main second anchor member body 1104 may have a generally rectangular shape (or have any other desired shape) when viewed in a direction normal to a substantially longitudinally extending surface of the main second anchor member body 1104, such as a second cam-contacting surface 1106. The main second anchor member body 1104 may be made of a hard plastic (e.g., polyurethane, or the like), a soft plastic (e.g., polyethylene, or the like), a metal (e.g., aluminum, or the like), or any other suitable material (e.g., a ceramic) or a combination of materials. The main second anchor member body 1104 may have a rigid or a semi-rigid configuration to selectively apply a laterally outwardly-oriented anchoring force to at least a portion of at least one elongate strand, as described in more detail below.

The main second anchor member body 1104 includes the second cam-contacting surface 1106 and a second strand-contacting surface 1108 laterally spaced on the main second anchor member body 1104 substantially opposite the second cam-contacting surface 1106. The main second anchor member body 1104 also includes a distal second anchor member surface 1110 longitudinally spaced from a proximal second anchor member surface 1112. The distal and proximal second anchor member surfaces 1110 and 1112 extend laterally between the second cam-contacting side 1106 and the second strand-contacting side 1108.

The second cam-contacting surface 1106 includes a first cam-receiving portion 1114 configured to selectively receive at least a portion of the first cam 1002, a second cam-receiving portion 1116 configured to selectively receive at least a portion of the second cam 1004, and a support member-contacting surface 1118 configured to selectively contact a portion of the support member 1010.

The first cam-receiving portion 1114 includes a first cam main body-receiving portion 1120 configured to receive at least a portion of the main first cam body 1012. The first cam-receiving portion 1114 also includes a first cam flange-support portion 1122 configured to support at least a portion of the second cam flange 1064. As shown in FIG. 15A, the second cam-receiving portion 1116 is positioned longitudinally adjacent the first cam-receiving portion 1114. It will be appreciated that the second cam-receiving portion 1116 may instead be longitudinally spaced from the first cam-receiving portion 1114.

Figure 19B:
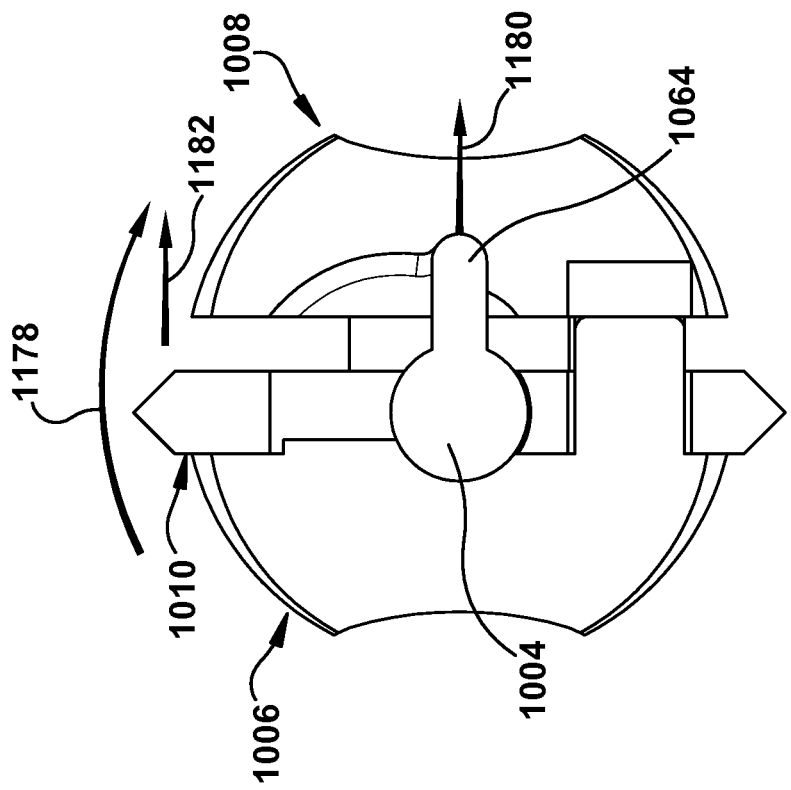
FIG. 19B is a cross-section taken along line 19-19 of FIG. 10 depicting an alternate configuration.
Figure 19A:
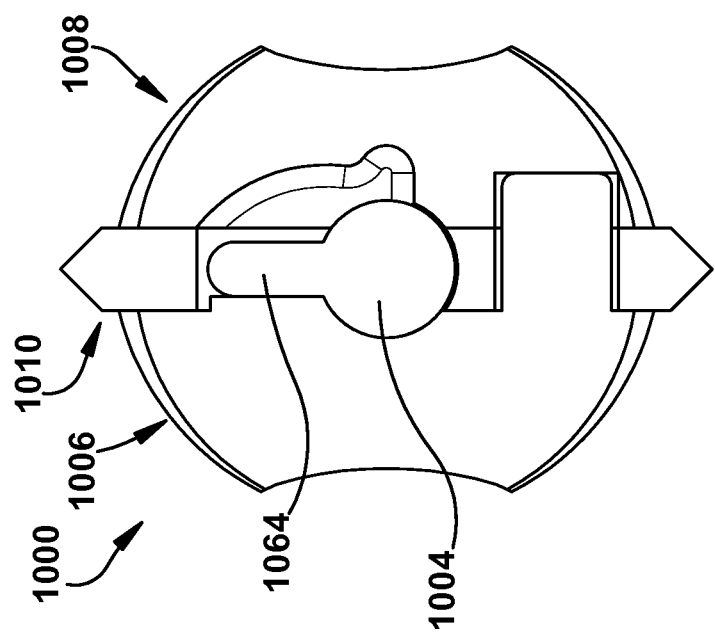
FIG. 19A is a cross-section taken along line 19-19 of FIG. 10.

The second cam-receiving portion 1116 includes a second anchor member stop 1124. As can be seen in FIGS. 19A-19B, the second anchor member stop 1124 protrudes outwardly from the second cam-receiving portion 1116. The second anchor member stop 1124 is configured to engage a portion of the second cam flange 1064, as described in more detail below. As shown in FIG. 15A, the second cam-receiving portion 1116 may also include at least one second anchor member detent 1126 disposed adjacent the second anchor member stop 1124. The at least one second anchor member detent 1126 is configured to at least temporarily engage a portion of the second cam flange 1064. The at least one second anchor member detent 1126 comprises a plurality of second anchor member detents 1126 disposed adjacent each other. It will be appreciated that each second anchor member detent 1126 may be radially spaced from the other second anchor member detents 1126.

The support member-contacting surface 1118 may include at least one second anchor member engagement member 1128, so named because each of the plurality of second anchor member engagement member 1128 contacts a portion of the support member 1010. The first anchor member engagement members 1096 can be disposed on at least a portion of the second cam-contacting side 1108. The second anchor member engagement members 1128, when present (a plurality of which will be described herein), are each configured to engage the corresponding plurality of first anchor member engagement members 1096, as described in more detail below. In one example, at least one of the plurality of second anchor member engagement members 1128 may be configured as a male member (e.g., a tab) or a female member (e.g., a recess) disposed on a portion of the second cam-contacting side 1108 and configured to telescopingly engage with a corresponding portion of the first anchor member 1006 to guide relative movement of the first and second anchor members 1006 and 1008. In another example, at least one of the plurality of second anchor member engagement members 1128' may be configured as an elastic tab configured to contract and expand into locking engagement with a corresponding portion of the first anchor member 1006, optionally in a telescoping manner, to prevent undesired lateral movement of the first and second anchor members 1006 and 1008.

As shown in FIG. 15B, the second strand-contacting surface 1108 includes a second strand-contacting portion 1130 configured to selectively contact at least a portion of at least one elongate strand. In one example, the second strand-contacting portion 1130 is substantially laterally centrally located on the second strand-contacting surface 1108. The second strand-contacting portion 1130 may be radially centrally offset on the second strand-contacting surface 1108. The second strand-contacting portion 1130 may have any other suitable location (e.g., centrally offset, vertically, etc.) on the second strand-contacting surface 1108. The second strand-contacting portion 1130 extends longitudinally between the proximal and distal second anchor member surfaces 1110 and 1112. The second strand-contacting portion 1130 has a generally planar profile; however, the second strand-contacting portion 1130 may have a generally convex profile, a generally concave profile, a combination profile, or any other suitable profile.

As shown in FIG. 15B, the second strand-contacting portion 1130 may include a plurality of second anchor member ribs 1131 configured to contact a portion of at least one elongate strand to prevent unwanted longitudinal movement of the at least one elongate strand. The second anchor member ribs 1131 extend laterally along substantially the entire second strand-contacting portion 1130; however, it will be appreciated that the second anchor member ribs 1131 may be present along only a portion of the length of the second strand-contacting portion 1130.

The second strand-contacting surface 1108 includes a second tunnel wall-contacting portion 1132 configured to selectively engage a portion of a tunnel wall. In one example, when the second strand-contacting portion 1130 is substantially radially centrally located on the second strand-contacting surface 1108, a pair of second tunnel wall-contacting portions 1132a and 1132b is disposed on opposing sides of the second strand-contacting portion 1130. The second tunnel wall-contacting portion 1132 may be radially centrally offset on opposing sides of the second strand-contacting portion 1130. The second tunnel wall-contacting portion 1132 may have any other suitable location (e.g., centrally offset, vertically, etc.) on the second strand-contacting surface 1108.

The second strand-contacting surface 1108 may also include a plurality of second anchor member ridges 1134 configured to contact a portion of a bone tunnel wall, as described in more detail below. The second anchor member ridges 1134 laterally extend along substantially the entire second tunnel wall-contacting portion 1132; however, it will be appreciated that the plurality of second anchor member ridges 1134 may be present along only a portion of the length of main second anchor member body 1104.

FIGS. 16A and 16B show an embodiment of the support member 1010. The support member 1010 is may be configured to support the first and second cams 1002 and 1004, and may be configured to guide lateral movement of the first and second anchor members 1006 and 1008.

In one example embodiment, the support member 1010 has a main support member body 1136. The main support member body 1136 may have generally trapezoidal shape (or have any other desired shape) as shown in FIG. 16A. The main support member body 1136 may be made of a hard plastic (e.g., polyurethane, or the like), a soft plastic (e.g., polyethylene, or the like), a metal (e.g., aluminum, or the like), or any other suitable material (e.g., a ceramic) or combination of materials. The main support member body 1136 may have a rigid or a semi-rigid configuration to support the first and second cams 1002 and 1004, and to guide lateral movement of the first and second anchor members 1006 and 1008, as described in more detail below.

The main support member body 1136 includes a first support member side 1138 and a second support member side 1140 laterally opposite the first support member side 1138. The main support member body 1136 also includes a distal support member surface 1142 longitudinally spaced from a proximal support member surface 1144. As shown in FIG. 16A, the distal and proximal support member surfaces 1142 and 1144 extend laterally between the first and second support member sides 1138 and 1140, and may taper slightly, to help with insertion. In one example, the proximal support member surface 1144 has a lateral length $D_1$ that is greater than a lateral length $D_2$ of the distal support member surface 1142.

The main support member body 1136 includes a first cam cut-out portion 1146 and a second cam cut-out portion 1148. The first and second cam cut-out portions 1146 and 1148 are sized and dimensioned to provide clearance to accommodate pivotal movement of the first and second cam flanges 1034 and 1064. As shown in FIG. 16A, the first and second cam cut-out portions 1146 and 1148 are positioned laterally offset from each other along the main support member body 1136. It will be appreciated that the first and second 1138 and 1140 may be positioned longitudinally and/or laterally aligned with each other.

The first cam cut-out portion 1146 has a distal first cam cut-out portion end 1150 and a proximal first cam cut-out portion end 1152. The first cam cut-out portion 1146 extends longitudinally into a portion of the main support member body 1136, and extends laterally between the first and second support member sides 1138 and 1140. The distal first cam cut-out portion end 1150 is disposed on a portion of the main support member body 1136 such that the distal first cam cut-out portion end 1150 is longitudinally interposed between the proximal support member surface 1144 and the second cam cut-out portion 1148. The proximal first cam cut-out portion end 1152 extends longitudinally through a portion of the proximal support member surface 1144. As shown in FIG. 16B, the proximal first cam cut-out portion end 1152 divides the proximal support member surface 1144 into a pair of proximal support member surfaces 1144a and 1144b disposed on opposing sides of the proximal first cam cut-out portion end 1152.

The second cam cut-out portion 1148 has a distal second cam cut-out portion end 1154 and a proximal second cam cut-out portion end 1156. The second cam cut-out portion 1148 extends longitudinally into a portion of the main support member body 1136, and extends laterally between the first and second support member sides 1138 and 1140. The distal second cam cut-out portion end 1154 is disposed on a portion of the main support member body 1136 such that the distal second cam cut-out portion end 1154 is interposed between the distal and proximal support member surfaces 1142 and 1144. As shown in FIG. 16A, the proximal second cam cut-out portion end 1156 is disposed longitudinally adjacent the distal first cam cut-out portion end 1150.

The main support member body 1136 also includes a plurality of anchor member-engagement member openings 1158 that extend laterally between the first and second support member sides 1138 and 1140. The anchor member-engagement member openings 1158 are configured to receive the corresponding plurality of second anchor member engagement members 1128 and/or the corresponding first anchor member engagement members 1096 when the first and second anchor members 1006 and 1008 are engaged with the main support member body 1136. That is, at least one of the first and second anchor member engagement members extends at least partially through at least one anchor member-engagement member opening to engage with another of the first and second anchor member engagement members.

The main support member body 1136 also includes first and second tunnel-engaging portions 1160 and 1162 that are laterally spaced from each other. The first and second tunnel-engaging portions 1160 and 1162 extend longitudinally from the proximal and distal support member surfaces 1142 and 1144. The first and second tunnel-engaging portions 1160 and 1162 are configured to engage a portion of a bone tunnel wall, as described in more detail below.

The anchoring apparatus 1000 is configured for use with a driver member 1164 that includes a main driver member body 1166. The driver member 1164 is configured to cause pivotal movement of the first and second cams 1002 and 1004. As shown in FIG. 17, the main driver member body 1166 of the driver member 1164 includes a first driver feature 1168 longitudinally spaced from a second driver feature 1170 along a longitudinal axis A' of the main driver member body 1166. The first driver feature 1168 is configured to engage the first cam driver-engaging feature 1022 and the second driver feature 1170 is configured to engage the second cam driver-engaging feature 1052. In the example embodiment shown, the first driver feature 1168 is configured as a male member with a hexagonal cross-sectional shape. Similarly, the second driver feature 1170 may be configured as a male member with a rectangular cross-sectional shape. However, one having ordinary skill in the art will be able to provide first and/or second driver features 1168 or 1170 configured for engagement as described with a particular anchoring apparatus 1000.

Referring back to FIGS. 10 and 11, the first cam 1002, the second cam 1004, the first anchor member 1006, the second anchor member 1008, and the support member 1010 are assembled with one another to form the anchoring apparatus 1000. In one example embodiment, the first cam 1002 and the second cam 1004 are placed at least partially within the corresponding first and second cam cut-out portions 1146 and 1148 of the support member 1010. The first and second anchor members 1006 and 1008 are placed adjacent to the corresponding first and second support member sides 1138 and 1140 of the support member 1010.

To begin assembly of the anchoring apparatus 1000, the second cam 1004 may be engaged with the support member 1010. The second cam 1004 is installed within the second cam cut-out portion 1148 such that the proximal second cam surface 1048 abuts the proximal second cam cut-out portion end 1156 and the distal second cam surface 1050 abuts the distal second cam cut-out portion end 1154. The second cam-receiving portion 1116 of the second anchor member 1008 and the second cam cut-out portion 1148 of the support member 1010 may cooperate to form a cavity that surrounds, and constrains undesired motion of, the second cam 1004. In one example, a temporary retaining feature (e.g., a ring, jig, clip, or the like) may be used to temporarily position and/or retain the second cam 1004 within the second cam cut-out portion 1148 during assembly of the anchoring apparatus 1000.

During or after installation of the second cam 1004 within the second cam cut-out portion 1148, the first cam 1002 is installed within the first cam cut-out portion 1146 such that the proximal first cam surface 1018 abuts the proximal first cam cut-out portion end 1152 and the distal first cam surface 1020 abuts the distal first cam cut-out portion end 1150. In one example, a temporary retaining feature (e.g., a ring, jig, clip, or the like) may be used to temporarily position and/or retain the first cam 1002 within the first cam cut-out portion 1146 during assembly of the anchoring apparatus 1000. It will be appreciated that the first and second cams 1002 and 1004 will usually be installed within the first and second cam cut-out portions 1146 and 1148 such that the first and second cam driver-engaging features 1022 and 1052 are substantially longitudinally aligned with each other. The first cam-receiving portion 1082 of the first anchor member 1006 and the first cam cut-out portion 1146 of the support member 1010 may cooperate to form a cavity that surrounds, and constrains undesired motion of, the first cam 1002.

During installation of the first cam 1002 within the first cam cut-out portion 1146, the first cam-engaging feature 1028 is engaged with the second cam-engaging feature 1058. The first cam-engaging feature 1028 may be slid over the second cam-engaging feature 1058 so that the second cam-engaging feature 1058 is received within the first cam-engaging feature 1028. To fit the first and second cams 1002 and 1004 together, the first cam-engaging feature 1028 is slid over the second cam-engaging feature 1058 so that the distal second cam-engaging feature end 1062 is received within the first cam-engaging feature 1028 and abuts the distal first cam-engaging feature end 1030, and the proximal second cam-engaging feature end 1060 abuts the proximal first cam-engaging feature end 1032.

The engagement of the first and second cam-engaging features 1028 and 1058 maintains the longitudinal arrangement of the first and second cams 1002 and 1004 so that the first and second cam driver-engaging features 1022 and 1052 are substantially longitudinally aligned. The engaged/assembled first and second cams 1002 and 1004 co-extend along, and are co-concentric with, the longitudinal axis A. It will be appreciated that, once the first and second cams 1002 and 1004 are engaged with the support member 1010, the longitudinal axis A of the anchoring apparatus 1000 extends through the aligned first and second driver-engaging features 1022 and 1052.

Once installed, the first and second cams 1002 and 1004 may each be rotated about an axis of rotation AR that is substantially laterally parallel to the longitudinal axis A. It will be appreciated that the axis of rotation AR may be substantially coaxial with longitudinal axis A. The first and second cam flanges 1034 and 1064 may pivotally move about the axis of rotation AR within the first and second cam cut-out portions 1146 and 1148.

Once the first and second cams 1002 and 1004 have been engaged with the support member 1010, the first and second anchor members 1006 and 1008 may be engaged with the support member 1010. In one example, the first cam-contacting surface 1074 is engaged with the first support member side 1132 so that the first cam-receiving portion 1082 receives the main first cam body 1012. The main second cam body 1042 engages the second cam main body-receiving portion 1092. The second cam flange 1064 abuts the second cam flange-support portion 1094. The support member-contacting surface 1086 abuts the first support member side 1132 so that the first anchor member engagement members 1096 extend through the corresponding anchor member-engagement member openings 1158 of the support member 1010.

The second anchor member 1008 may be engaged with the support member 1010 in a similar manner as the first anchor member 1006. However, it will be appreciated that the second anchor member 1008 may be at least partially engaged with the support member 1010 before, during, or after the engagement of at least a portion of the first anchor member 1006 and the support member 1010. The second cam-receiving portion 1116 receives a portion of the main second cam body 1042. The second cam-contacting surface 1106 is engaged with the second support member side 1134 so that the first cam main body-receiving portion 1120 receives the main first cam body 1012. The second cam flange 1064 abuts the first cam flange-support portion 1122. The support member-contacting surface 1118 abuts the second support member side 1134 so that the second anchor member engagement members 1128 extend through the corresponding anchor member-engagement member openings 1158 of the support member 1010 and engage the corresponding first anchor member engagement members 1096 in a male-female telescoping connection, as shown, or in any other suitable manner.

Once the anchoring apparatus 1000 has been assembled as discussed above, the first and second cams 1002 and 1004 are arranged longitudinally adjacent each other along the longitudinal axis A. The first and second strand-contacting surfaces 1076 and 1108 are spaced laterally apart by a local apparatus distance L. In reference to the anchoring apparatus 1000, the term "local apparatus distance" (and variants thereof) refers to a lateral distance between the first and second strand-contacting surfaces 1076 and 1108 within an area defined by the anchoring apparatus 1000. The support member 1010 is interposed between, and supportively connected to, the support member-contacting surfaces 1086 and 1118 of the first and second anchor members 1006 and 1008, respectively. The first and second anchor member engagement members 1096 and 1128 of the first and second anchor members 1006 and 1008, respectively, are engaged with each other via the anchor member-engagement member openings 1158 of the support member 1010.

The anchoring apparatus 1000 may be configured for use with the driver member 1164 shown in FIG. 17. As shown in the configuration of FIG. 18A, the first cam flange 1034 is initially spaced from the first anchor member 1006. The first driver feature 1168 may be engaged with the first cam driver-engaging feature 1022. Although not shown in FIGS. 18A-18B, the first driver feature 1168 may be advanced through the first cam driver-engaging feature 1022 until the first driver feature 1168 abuts the distal first cam driver-engaging feature end 1026. The driver member 1164 may then be rotated in a first pivotal direction 1172 about the axis of rotation AR to engage with the first cam driver-engaging feature 1022 and thereby cause pivotal movement of the first cam flange 1034. As shown, the first pivotal direction 1172 is a clockwise direction in the orientation of FIGS. 18A-18B; however, it will be appreciated that the first pivotal direction 1172 may be a counter-clockwise direction, depending on the configuration of the anchoring apparatus 1000.

The rotation of the driver member 1164 in the first pivotal direction 1172 causes pivotal movement of the first cam 1002 in the first pivotal direction 1172 due to the engagement between the first driver feature 1168 and the distal first cam driver-engaging feature end 1026. The pivotal movement of the first cam 1002 causes the first cam flange 1034 to apply a first laterally-outwardly directed force 1174 to the first cam-contacting surface 1074. As shown in the configuration of FIG. 18B, the first anchor member-contacting surface 1036 contacts the first anchor member stop 1088 and applies the first laterally-outwardly directed force 1174 thereto. The first laterally-outwardly directed force 1174 causes substantially lateral movement of the first anchor member 1006 in a first lateral direction 1176, optionally guided by the telescoping relative motion of the first and second anchor member engagement members 1096 and 1128 within the anchor member-engagement member openings 1158.

Once the first anchor member 1006 is positioned the first anchor member 1006 in a desired lateral position relative to the longitudinal axis A, the first driver feature 1168 is disengaged from the first cam driver-engaging feature 1022. The second driver feature 1170 is then engaged with the second cam driver-engaging feature 1052. The second driver feature 1170 may be, for example, advanced past the first cam driver-engaging feature 1022 and into the second cam driver-engaging feature 1052 until the second driver feature 1170 abuts the distal second cam-engaging feature end 1060.

As shown in the configuration of FIG. 19A, the second cam flange 1064 is initially spaced from the second anchor member 1008. The driver member 1164 may then be rotated in a second pivotal direction 1178 about the axis of rotation AR to engage with the second cam driver-engaging feature 1052 and thereby cause pivotal movement the second cam flange 1064. As shown, the second pivotal direction 1178 is a clockwise direction in the orientation of FIGS. 19A-19B; however it will be appreciated that the second pivotal direction 1178 may be a counter-clockwise direction, depending on the configuration of the anchoring apparatus 1000. It will be appreciated that the first and second pivotal directions 1172 and 1178 may each be a counter-clockwise or a clockwise direction, or that one of the first and second pivotal directions 1172 and 1178 may be a counter-clockwise direction and the other of the first and second pivotal directions 1172 and 1178 may be a clockwise direction.

The rotation of the driver member 1164 in the second pivotal direction 1178 causes pivotal movement of the second cam 1004 in the second pivotal direction 1178 due to the engagement between the second driver feature 1170 and the proximal second cam driver engagement feature 1056. The pivotal movement of the second cam 1004 causes the second cam flange 1064 to apply a second laterally-outwardly directed force 1180 to the second cam-contacting surface 1106. As shown in the configuration of FIG. 19B, the second anchor member-contacting surface 1066 contacts the second anchor member stop 1124 and applies the second laterally-outwardly directed force 1180 thereto. The second laterally-outwardly directed force 1180 causes substantially lateral movement of the second anchor member 1008 in a second lateral direction 1182, optionally guided by the telescoping relative motion of the first and second anchor member engagement members 1096 and 1128 within the anchor member-engagement member openings 1158.

In other words, the first and second cams 1002 and 1004 may each have a non-actuated cam state shown in FIGS. 18A and 19A, respectively, in which the first and second cam flanges 1034 and 1064 are spaced from the corresponding first and second anchor members 1006 and 1008. The first and second cams 1002 and 1004 may each transition to an actuated cam state from their respective non-actuated cam states, in which the first and second cam flanges 1034 and 1064 are engaged with the corresponding first and second anchor member stops 1088 and 1124, as shown in FIGS. 18B and 19B, respectively.

Similarly, the first and second anchor members 1006 and 1008 may each have a respective non-actuated anchor member state shown in FIGS. 18A and 19A, respectively, in which the first and second anchor members 1006 and 1008 are each spaced from the corresponding first and second cam flanges 1034 and 1064. The first and second anchor members 1006 and 1008 may transition from their respective non-actuated anchor member states to an actuated anchor member state in which the first and second anchor member stops 1088 and 1124 engage the corresponding first and second cam flanges 1034 and 1064, as shown in FIGS. 18B and 19B, respectively.

Figure 20:
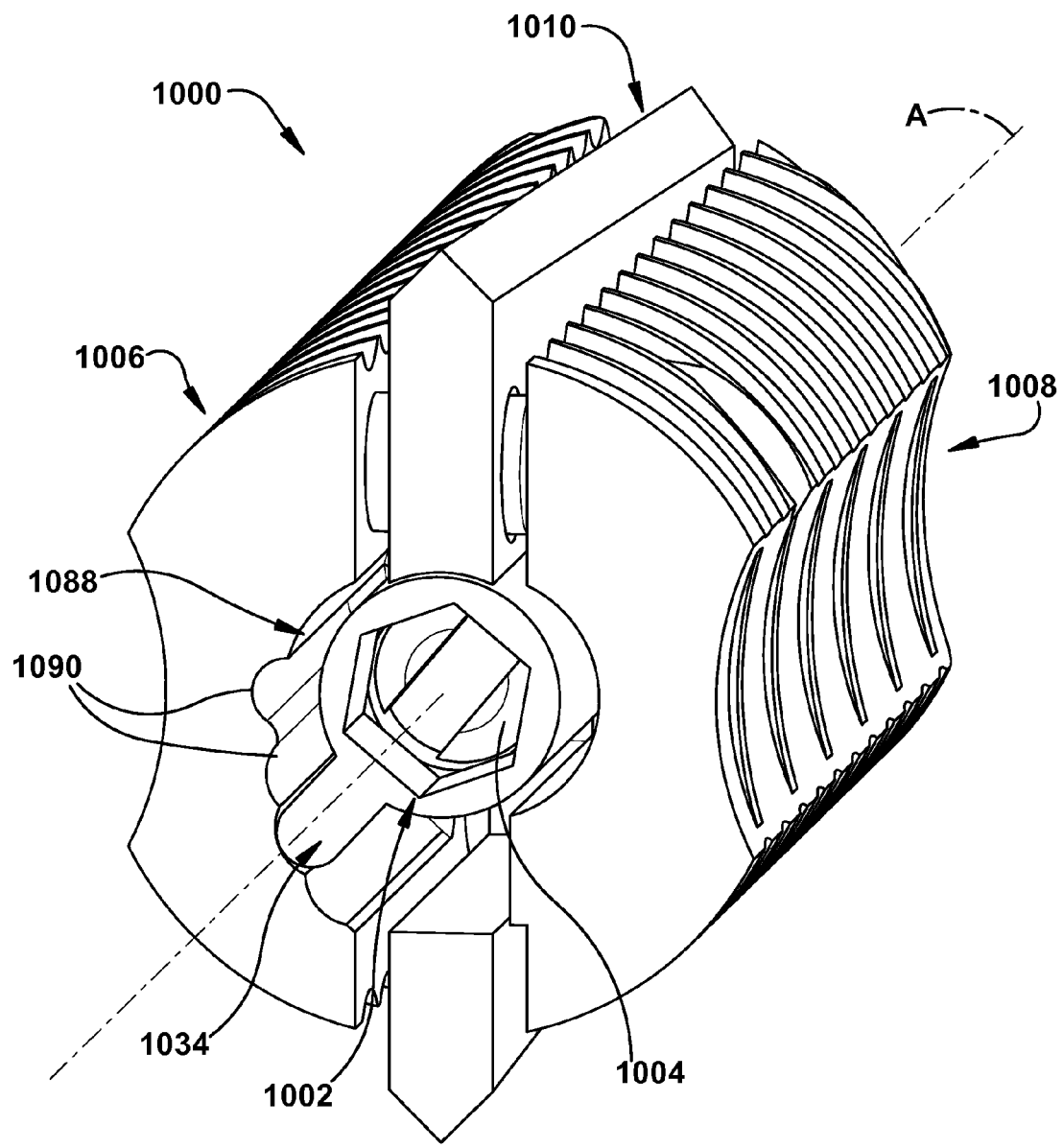
FIG. 20 is a front perspective view of an alternative configuration of the embodiment of FIG. 10.

In another example embodiment, the first and second cam flanges 1034 and 1064 can engage the first and second anchor member detents 1090 and 1126, when present, respectively, during pivotal movement of the first and second cams 1002 and 1004. As shown in FIG. 20, the first cam flange 1034 engages one of the first anchor member detents 1090 when the first cam 1002 pivotally moves in the first pivotal direction 1172 upon rotation of the driver member 1164. The first cam flange 1034 may engage the first anchor member detents 1090 is a ratchet-type motion as the first cam flange 1034 moves in the first pivotal direction 1172 towards the first anchor member stop 1088. In one example, the pivotal movement of the first cam flange 1034 in the first pivotal direction 1172 causes the first cam flange 1034 to rub against the first cam-receiving portion 1082 to anchor the first cam flange 1034 against the first cam-contacting surface 1074 via frictional engagement.

The second cam flange 1064 engages one of the second anchor member detents 1126 (not shown in FIG. 20) when the second cam 1004 pivotally moves in the second pivotal direction 1178 upon rotation of the driver member 1164. The second cam flange 1064 may engage the second anchor member detents 1126 in a ratchet-type motion as the second cam flange 1064 moves in the second pivotal direction 1178 towards the second anchor member stop 1124. In one example, the pivotal movement of the second cam flange 1064 in the second pivotal direction 1178 causes the second cam flange 1064 to rub against the second cam-receiving portion 1116 to anchor the second cam flange 1064 against the second cam-contacting surface 1106 via frictional engagement.

FIGS. 21A-21D depict a sequence of use for the anchoring apparatus 1000. The anchoring apparatus 1000 is configured for anchoring first and second elongate strands 1184 and 1186 within a longitudinal bone tunnel 1188 against a bone tunnel wall 1190. Although the following sequence will be discussed with only the first and second elongate strands 1184 and 1186, it will be appreciated that any number of elongate strands may be used in conjunction with the anchoring apparatus 1000.

Figure 21A:
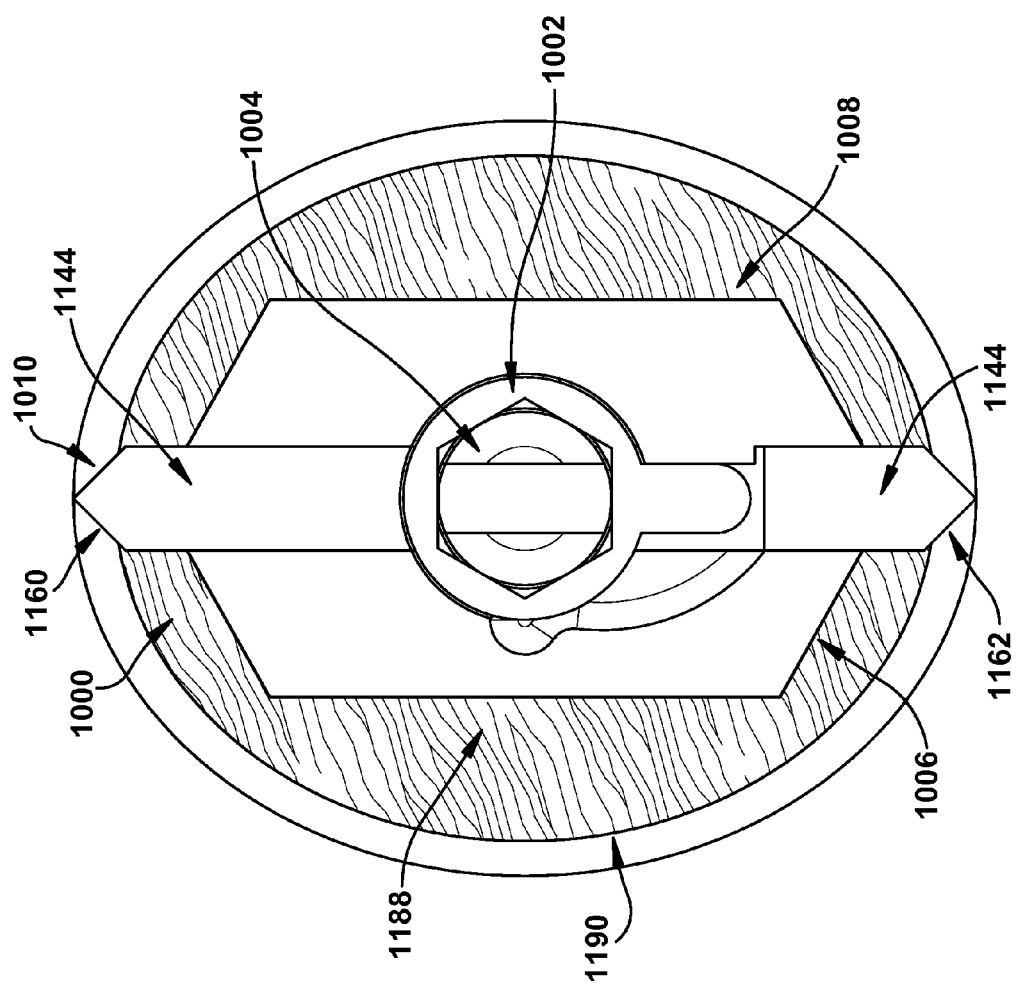

The anchoring apparatus 1000 is initially placed into the bone tunnel 1188. As shown in FIG. 21A, the first and second tunnel engaging portions 1160 and 1162 may be inserted into the bone tunnel 1188 and may penetrate into portions of the bone tunnel wall 1190 to orient and stabilize the anchoring apparatus 1000 relative to the bone tunnel 1188. It will be appreciated that the tapered configuration of the distal and proximal support member surfaces 1142 and 1144, when present, accommodates the insertion of the anchoring apparatus 1000 into the bone tunnel 1188 prior to the engagement of the first and second tunnel engaging portions 1160 and 1162 with the bone tunnel wall 1190. As shown in FIG. 21A, the first and second strand-contacting surfaces 1076 and 1108 are initially laterally spaced from the first and second tunnel engaging portions 1160 and 1162. The anchoring apparatus 1000 is inserted a desired longitudinal distance into the bone tunnel 1188. When the anchor apparatus 1000 is inserted into the bone tunnel 1188, the tunnel wall may be engaged with the support member (e.g., through the first and second tunnel-engaging portions 1160 and 1162 "digging in" to the tunnel wall) to resist movement of the anchor apparatus within the longitudinal tunnel.

Before, during, or after the anchoring apparatus 1000 is placed within the bone tunnel 1188, the first and second elongate strands 1184 and 1186 are advanced into the bone tunnel 1188. As shown in FIG. 21B, the first and second elongate strands 1184 and 1186 are positioned between the corresponding first and second strand-contacting surfaces 1076 and 1108 and a portion of the bone tunnel wall 1190. The first elongate strand 1184 is in a first elongate strand position in which the first elongate strand 1184 is positioned substantially parallel to the longitudinal axis A and is interposed laterally between the bone tunnel wall 1190 and a portion of the first strand-contacting surface 1076. The second elongate strand 1186 is in a second elongate strand position, in which the second elongate strand 1186 positioned substantially parallel to the longitudinal axis A and is interposed laterally between the bone tunnel wall 1190 and a portion of the second strand-contacting surface 1108.

When the first and second elongate strands 1184 and 1186 are in the corresponding first and second elongate strand positions laterally adjacent the first and second strand-contacting surfaces 1076 and 1108, respectively, the local apparatus distance L may be a local minimum apparatus distance $L_{min}$ at the first and second elongate strand positions and is a local maximum apparatus distance $L_{max}$ at a location laterally spaced from both of the first and second elongate strand positions. However, it will be appreciated that when the first and second strand-contacting surfaces 1076 and 1108 have a planar configuration or a concave configuration, the local apparatus distance L is a local maximum apparatus distance $L_{max}$ at the first and second elongate strand positions and may be a local minimum apparatus distance $L_{min}$ at a location laterally spaced from both of the first and second elongate strand positions.

Figure 21C:
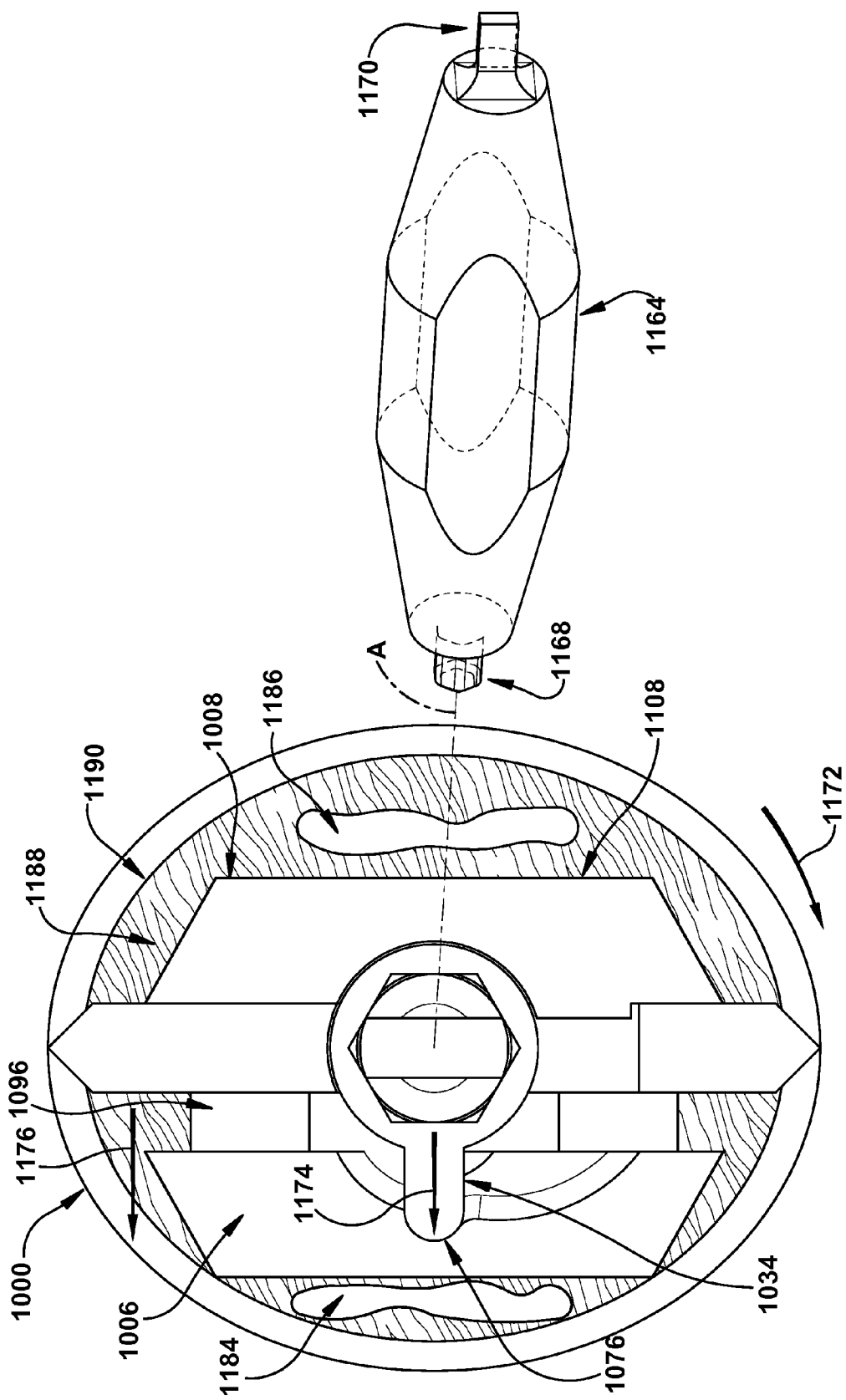

Once the first and second elongate strands 1184 and 1186 are positioned within the bone tunnel 1188, the first driver feature 1168 may be engaged with the first cam driver-engaging feature 1022 to rotate the first cam 1002 about the axis of rotation AR in the first pivotal direction 1172. As shown in FIG. 21C, the driver member 1164 is rotated in the first pivotal direction 1172 (i.e., counter-clockwise in the orientation of FIG. 21C) so that the first cam flange 1034 moves in the first pivotal direction 1172. The first anchor member-contacting surface 1036 then contacts the first anchor member stop 1088 and applies the first laterally-outwardly directed force 1174 to the first cam-contacting surface 1074.

Consequently, the first strand-contacting surface 1076 moves laterally in the first lateral direction 1176 towards a portion of the bone tunnel wall 1190. The first strand-contacting surface 1076 may optionally continue to move in the first lateral direction 1176 until at least a portion of the first tunnel wall-contacting portion 1100 contacts a portion of the bone tunnel wall 1190. Although not shown in FIG. 21C, the first tunnel wall-contacting portion 1100 may be configured to extend longitudinally along the bone tunnel wall 1190 such that the first tunnel wall-contacting portion 1100 longitudinally contacts the bone tunnel wall 1190. The first anchor member ridges 1102 may compress against a portion of the bone tunnel wall 1190 to provide an anti-slip engagement between the portion of the bone tunnel wall 1190 and the first strand-contacting surface 1076.

When the first tunnel wall-contacting portion 1100 engages the bone tunnel wall 1190, the first strand-contacting portion 1098 anchors the first elongate strand 1184 against the bone tunnel wall 1190. As a result, a frictional engagement of the first elongate strand 1184 is produced between the first strand-contacting surface 1076 and the bone tunnel wall 1190 whereby the first strand-contacting surface 1076 anchors the first elongate strand 1184 against the bone tunnel wall 1190 to resist longitudinal motion of the first elongate strand 1184. The first anchor member ribs 1099 prevent longitudinal movement of the first elongate strand 1184.

In one example, the first anchor member engagement members 1096 may be sized and dimensioned so that the first anchor member engagement members 1096 are maintained within the anchor member-engagement member openings 1158 when the first tunnel wall-contacting portion 1100 contacts a portion of the bone tunnel wall 1190. This configuration of the first anchor member engagement members 1096 prevents further lateral movement of the first anchor member 1006 while maintaining the engagement of the first anchor member 1006 with the support member 1010. In another example, at least one of the first anchor member engagement members 1096' may resiliently expand into locking engagement with a corresponding anchor member-engagement member opening 1158. As a result, further lateral movement of the first anchor member 1006 is prevented, and the first anchor member 1006 is thereby prevented from disengaging the support member 1010.

Once the first elongate strand 1184 is at least partially anchored against the bone tunnel wall 1190, the second elongate strand 1186 remains in the second elongate strand position and can be adjusted as desired by the user before at least partial anchoring via actuation of the second anchor member 1008. It will thus be appreciated that the engagement of the first elongate strand 1184 with the bone tunnel wall 1190 may be temporally spaced from the engagement of the second elongate strand 1186 with the bone tunnel wall 1190. After the first elongate strand 1184 is at least partially anchored against the bone tunnel wall 1190, the first driver feature 1168 is disengaged from the first cam driver-engaging feature 1022. The second driver feature 1170 is then advanced past the first cam driver-engaging feature 1022 and engaged with the second cam driver-engaging feature 1052. As shown in FIG. 21D, the driver member 1164 (omitted from this view for clarity) is rotated in the second pivotal direction 1178 so that the second cam flange 1064 moves in the second pivotal direction 1178. It will be appreciated that, although the second pivotal direction 1178 is the same as the first pivotal direction 1172 (i.e., clockwise), the second pivotal direction 1178 may be different (i.e., counter-clockwise) from the first pivotal direction 1172. It will also be appreciated that the first cam flange 1034 may engage at least one of the first anchor member detents 1090 prior to engagement of the first cam flange 1034 with the first anchor member stop 1088. The second anchor member-contacting surface 1066 then contacts the second anchor member stop 1124 and applies the second laterally-outwardly directed force 1180 to the second cam-contacting surface 1106.

Consequently, the second strand-contacting surface 1108 moves laterally in the second lateral direction 1182 towards the bone tunnel wall 1190. The second strand-contacting surface 1108 may optionally continue to move in the second lateral direction 1182 until at least a portion of the second tunnel wall-contacting portion 1132 contacts a portion of the bone tunnel wall 1190. Although not shown in FIG. 21D, the second tunnel wall-contacting portion 1132 may be configured to extend longitudinally along the bone tunnel wall 1190 such that the second tunnel wall-contacting portion 1132 longitudinally contacts the bone tunnel wall 1190. The second anchor member ridges 1134 may compress against a portion of the bone tunnel wall 1190 to provide an anti-slip engagement between the portion of the bone tunnel wall 1190 and the second strand-contacting surface 1108.

When the second tunnel wall-contacting portion 1132 engages the bone tunnel wall 1190, the second strand-contacting portion 1130 anchors the second elongate strand 1186 against the bone tunnel wall 1190. As a result, a frictional engagement of the second elongate strand 1186 is produced between the second strand-contacting surface 1108 and the bone tunnel wall 1190 whereby the second strand-contacting surface 1108 anchors the second elongate strand 1186 against the bone tunnel wall 1190 to resist longitudinal motion of the second elongate strand 1186. The second anchor member ribs 1131 prevent longitudinal movement of the second elongate strand 1186.

In one example, the second anchor member engagement members 1128 are sized and dimensioned so that the second anchor member engagement members 1128 are maintained within the anchor member-engagement member openings 1158 when the second tunnel wall-contacting portion 1132 contacts a portion of the bone tunnel wall 1190. This configuration of the second anchor member engagement members 1128 prevents further lateral movement of the second anchor member 1008 while maintaining the engagement of the second anchor member 1008 with the support member 1010. At least one of the second anchor member engagement members 1128' may resiliently expand into locking engagement with a corresponding anchor member-engagement member opening 1158. As a result, further lateral movement of the second anchor member 1008 is prevented, and the second anchor member 1008 is thereby prevented from disengaging the support member 1010.

In one example, the second cam 1004 may be rotated prior to the rotation of the first cam 1002, and the second anchor member 1008 may engage the bone tunnel wall 1190 prior to the engagement of the first anchor member 1006 and the bone tunnel wall 1190. It will be appreciated that before, during, and after rotation of each of the first and second cams 1002 and 1004, each of the first and second elongate strands 1184 and 1186 are concurrently located in the corresponding first and second elongate strand positions. Since the first and second cams 1002 and 1004 may be rotated independent of one another, the frictional engagement of the first elongate strand 1184 between the bone tunnel wall 1190 and the first strand-contacting surface 1076 may be temporally spaced apart from the frictional engagement of the second elongate strand 1186 between the bone tunnel 1188 and the second strand-contacting surface 1108. Accordingly, the anchoring apparatus 1000 may be a sequentially-actuated graft anchor apparatus.

Alternatively, the driver member 1164 may be provided to actuate both the first and second cams 1002 and 1004 simultaneously. In one example, the driver member 1164 may be configured to simultaneously engage the first and second driver-engagement members 1028 and 1058. Upon rotation of the driver member 1164, each of the first and second cams 1002 and 1004 move pivotally and engage the corresponding first and second anchor members 1006 and 1008. Accordingly, the anchoring apparatus 1000 may be a simultaneously-actuated graft anchor apparatus.

The specific methods described above for using the anchoring apparatus 1000 are merely illustrative; one of ordinary skill in the art could readily determine any number of tools, sequences of steps, or other means/options for placing the above-described apparatus, or components thereof, into positions substantially similar to those shown and described herein.

While aspects of the present invention have been particularly shown and described with reference to the preferred embodiment above, it will be understood by those of ordinary skill in the art that various additional embodiments may be contemplated without departing from the spirit and scope of the present invention. For example, the specific method described above for installing the apparatus 100 is merely illustrative; one of ordinary skill in the art could readily determine any number of tools, sequences of steps, or other means/options for placing the apparatus, or components thereof, into positions substantively similar to those shown and described herein. Any of the described structures and components could be integrally formed or separately provided of any suitable material or combinations of materials; however, the chosen material(s) should be biocompatible for most applications of the present invention. Though certain components described herein are shown as having specific geometric shapes (e.g., the cylindrical sleeve 108" and actuating member 128" of the FIG. 5 embodiment), all structures of the present invention may have any suitable shapes, sizes, configurations, relative relationships, cross-sectional areas, or any other physical characteristics as desirable for a particular application of the present invention. The apparatus 100 could be configured to collapse and deploy in any suitable manner. The apparatus 100 could have a structure, or portions thereof, with inflation/expansion, pliability, rigidity, solidity, hollowness, or any other physical properties as desired for a particular application of the present invention. The apparatus 100 may be placed at the anchoring site in any suitable manner; for example, portions of the apparatus could be placed via open surgery and/or advanced through a previously installed sheath, trocar, or tube which terminates near the anchoring site. The inner lumen liner 542, when present, may be shaped to include the asymmetrically offset profile and transfer forces from the actuating member 128 to the sleeve outer surface 110 to anchor a plurality of graft ligaments. A description of a "circumference" or "radial" direction with reference to a curvilinear structure should be interpreted as meaning an analogous feature or direction for a structure which includes non-curvilinear portions. When there are more than two graft ligaments to be anchored, the asymmetrically offset profile may include some symmetries which allow more than one, but not all, of the graft ligaments to be frictionally engaged at substantially the same time. Any portion of the sleeve outer surface 110 may conform to the shape of the adjacent bone tunnel 106 to any degree, during any stage of the deployment and use of the apparatus 100, as desired by the user, and the material of the sleeve 108 may be chosen to create a desired degree of conformation. At least a portion of the actuating member 128 may be longitudinally inserted into the sleeve inner lumen 116 at any time before, while, or after the graft ligaments 102 and 104 and sleeve 108 are arranged within the bone tunnel 106. An external tool or structure (not shown) may be used to manipulate and/or steady one or both of the sleeve 108 and actuating member 128 during use. Sleeve aggregating members 440 could be located at either or both of the proximal and distal sleeve ends 112 and 114 for an apparatus 100 having a plurality of sleeve segment members 436. A device or method incorporating any of these features should be understood to fall under the scope of the present invention as determined based upon the claims below and any equivalents thereof.

Other aspects, objects, and advantages of the present invention can be obtained from a study of the drawings, the disclosure, and the appended claims.

Having described the invention, we claim:

1. An apparatus for anchoring at least two elongate strands within a longitudinal tunnel, the tunnel having a tunnel wall, the apparatus comprising:
   a longitudinal axis;
   at least two cams arranged longitudinally adjacent each other along the longitudinal axis;
   a first anchor member having a first anchor member body, the first anchor member being laterally spaced from the longitudinal axis and extending in a first lateral direction with respect to the longitudinal axis, the first anchor member including a first cam-contacting surface disposed on a portion of the first anchor member body and a first strand-contacting surface disposed on a portion of the first anchor member body laterally spaced from the first cam-contacting surface, the first cam-contacting surface being selectively operatively connected to a first one of the at least two cams;
   a second anchor member having a second anchor member body, the second anchor member being laterally spaced from the longitudinal axis and extending in a second lateral direction with respect to the longitudinal axis, the second lateral direction being different from the first lateral direction, the second anchor member including a second cam-contacting surface disposed on a portion of the second anchor member body and a second strand-contacting surface disposed on a portion of the second anchor member body laterally spaced from the second cam-contacting surface, the second cam-contacting surface being selectively operatively connected to a second one of the at least two cams;
   wherein at least a portion of at least one first elongate strand is positioned parallel to the longitudinal axis and is interposed laterally between the tunnel wall and at least a portion of the first strand-contacting surface, and at least a portion of at least one second elongate strand is positioned parallel to the longitudinal axis and is interposed laterally between the tunnel wall and at least a portion of the second strand-contacting surface;
   wherein rotation of a selected cam of the at least two cams about an axis of rotation which is at least one of parallel to and coextensive with the longitudinal axis produces pivotal movement of at least a portion of the selected cam about the longitudinal axis, the pivotal movement of the portion of the selected cam causing the pivotally-moving portion of the selected cam to selectively apply a force from the selected cam to at least a portion of a corresponding first or second cam-contacting surface to urge the corresponding first or second strand-contacting surface away from the longitudinal axis in the corresponding first or second lateral direction, thereby producing frictional engagement of at least one corresponding elongate strand with both the tunnel wall and the corresponding first or second strand-contacting surface.

2. The apparatus of claim 1, wherein rotation of another cam of the at least two cams about the axis of rotation produces pivotal movement of at least a portion of the other cam about the longitudinal axis, the pivotal movement of the portion of the other cam causing the pivotally-moving portion of the other cam to selectively apply a force from the other cam to at least a portion of a corresponding first or second cam-contacting surface to urge the corresponding first or second strand-contacting surface away from the longitudinal axis in the corresponding first or second lateral direction, thereby producing frictional engagement of at least one corresponding elongate strand with both the tunnel wall and the corresponding first or second strand-contacting surface.

3. The apparatus of claim 1, wherein the first and second strand-contacting surfaces are spaced laterally apart by a local apparatus distance, the at least one first and second elongate strands being positioned laterally adjacent the corresponding first and second strand-contacting surfaces at corresponding first and second elongate strand positions so that the apparatus distance is a local minimum apparatus distance at the elongate strand positions and is a local maximum apparatus distance at a location laterally spaced from both of the elongate strand positions.

4. The apparatus of claim 1, including a support member disposed between, and supportively connected to, at least a portion of both of the first and second anchor members, wherein the at least two cams are pivotally connected to the support member, the support member engaging at least a portion of both the first and second anchor members such that the engagement of the support member with the first and second anchor members guides lateral motion of each of the first and second strand-contacting surfaces in the corresponding first and second lateral directions when the at least two cams are rotated.

5. The apparatus of claim 4, wherein the first anchor member includes at least one first anchor member engagement member, the second anchor member includes at least one second anchor member engagement member, the support member includes at least one anchor member-engagement member opening extending laterally therethrough, and at least one of the first and second anchor member engagement members extends at least partially through at least one anchor member-engagement member opening to engage with another of the first and second anchor member engagement members.

6. The apparatus of claim 1, wherein the frictional engagement of a selected one of the first and second elongate strands located between the tunnel wall and a selected one of the first and second strand-contacting surfaces corresponding to the selected one of the first and second elongate strands upon rotation of the selected cam is temporally spaced apart from the frictional engagement of at least one other selected one of the first and second elongate strands located between the tunnel wall and the other of the first and second strand-contacting surfaces corresponding to the other selected one of the first and second elongate strands upon rotation of another cam of the at least two cams, the temporal spacing being provided by independent rotation of the selected cam and the other cam.

7. The apparatus of claim 1, wherein the longitudinal tunnel is a bone tunnel and the apparatus is a sequentially-actuated graft anchor apparatus for use in anchoring at least two longitudinally extending ones of the at least two elongate strands within the bone tunnel during replacement of a native tissue.

8. The apparatus of claim 7, wherein a selected one of the elongate strands is at least one of a native and a replacement anterior cruciate ligament ("ACL").

9. The apparatus of claim 1, wherein before, during, and after rotation of at least one of the first and second cams about the longitudinal axis, all of the elongate strands are concurrently located laterally adjacent corresponding ones of the first and second strand-contacting surfaces.

10. The apparatus of claim 1, wherein the first anchor member includes at least one first anchor member engagement member, the second anchor member includes at least one second anchor member engagement member, and the first and second anchor member engagement members are configured to telescopingly engage to guide relative movement of the first and second anchor members.

11. The apparatus of claim 1, wherein the first anchor member includes at least one first anchor member engagement member, the second anchor member includes at least one second anchor member engagement member, and a chosen one of the first and second anchor member engagement members includes an elastic tab configured to contract and expand into locking engagement with a corresponding portion of the other one of the first and second anchor member engagement members to prevent undesired lateral movement of the first and second anchor members.

12. The apparatus of claim 1, wherein a first cam of the at least two cams is selectively operatively engaged with the first cam-contacting surface, the first cam having a first cam flange and a first cam driver-engaging feature, and a second cam of the at least two cams is selectively operatively engaged with the second cam-contacting surface, the second cam having a second cam flange and a second cam driver-engaging feature.

13. The apparatus of claim 12, wherein the first cam is rotated relative to the longitudinal axis in a first pivotal direction and the second cam is rotated relative to the longitudinal axis in a second pivotal direction that is opposite the first pivotal direction.

14. A system for anchoring at least two elongate strands within a longitudinal tunnel, the system comprising the apparatus of claim 5 and an actuating member having a first driver feature and a second driver feature, wherein the force from the selected cam is a corresponding one of a first laterally outwardly-directed force and a second laterally outwardly-directed force, and wherein the first driver feature is configured to engage the first cam driver-engaging feature to rotate the first cam upon rotation of the actuating member, thereby causing the first cam flange to apply the first laterally outwardly-directed force to the first cam-contacting surface to urge the first strand-contacting surface away from the longitudinal axis in the first lateral direction, and the second driver feature is configured to engage the second cam driver-engaging feature to rotate the second cam upon rotation of the actuating member, thereby causing the second cam flange to apply the second laterally outwardly-directed force to the second cam-contacting surface to urge the second strand-contacting surface away from the longitudinal axis in the second lateral direction.

\* \* \* \* \*